United States Patent
Janardhan et al.

(10) Patent No.: US 9,179,931 B2
(45) Date of Patent: *Nov. 10, 2015

(54) SHAPE-SET TEXTILE STRUCTURE BASED MECHANICAL THROMBECTOMY SYSTEMS

(71) Applicant: Insera Therapeutics, Inc., Sacramento, CA (US)

(72) Inventors: Vallabh Janardhan, Dallas, TX (US); Vikram Janardhan, Sacramento, CA (US)

(73) Assignee: Insera Therapeutics, Inc., Sacramento, CA (US)

( * ) Notice: Subject to any disclaimer, the term of this patent is extended or adjusted under 35 U.S.C. 154(b) by 246 days.

This patent is subject to a terminal disclaimer.

(21) Appl. No.: 14/012,161

(22) Filed: Aug. 28, 2013

(65) Prior Publication Data

US 2014/0277081 A1    Sep. 18, 2014

Related U.S. Application Data

(63) Continuation of application No. 13/952,982, filed on Jul. 29, 2013, now Pat. No. 8,679,150.

(60) Provisional application No. 61/798,540, filed on Mar. 15, 2013.

(51) Int. Cl.
*A61M 29/00* (2006.01)
*A61B 17/3207* (2006.01)
(Continued)

(52) U.S. Cl.
CPC ....... *A61B 17/320725* (2013.01); *A61B 17/221* (2013.01); *A61B 17/22031* (2013.01); *A61B 17/22032* (2013.01); *A61B 2017/2217* (2013.01);

(Continued)

(58) Field of Classification Search
CPC .............. A61B 17/22031; A61B 2017/22034; A61B 17/22032; A61B 17/221; A61B 17/3207; A61B 17/320725; A61B 17/32075; A61B 2019/5466

See application file for complete search history.

(56) References Cited

U.S. PATENT DOCUMENTS 3,378,282 A    4/1968  Demler, Sr.
3,381,114 A    4/1968  Nakanuma
(Continued)

FOREIGN PATENT DOCUMENTS

EP    0 521 595    1/1993
EP    1 676 545    7/2006
(Continued)

OTHER PUBLICATIONS

6th Annual MedTech Investing Conference, "Venture Capital and Private Equity Investing in Medical Devices and Healthcare Technologies," May 16-17, 2007.
(Continued)

*Primary Examiner* — Jonathan W Miles
(74) *Attorney, Agent, or Firm* — Knobbe Martens Olson & Bear, LLP

(57) ABSTRACT

A biomedical shape-set textile structure based mechanical thrombectomy systems and methods are described. In one of the embodiments, the mechanical thrombectomy device can be customized to the length of the clot in each patient. In one of the embodiments, the mechanical thrombectomy device because of the textile structure has a very low overall profile or thickness that is less than 0.0125 inches (0.317 mm) and therefore can be deployed within microcatheters with inner lumen diameter as small as 0.014 inches (0.355 mm).

20 Claims, 54 Drawing Sheets

(51) Int. Cl.
*A61B 17/221* (2006.01)
*A61B 17/22* (2006.01)
*A61B 19/00* (2006.01)

(52) U.S. Cl.
CPC .............. *A61B 2017/22034* (2013.01); *A61B 2019/5466* (2013.01)

(56) References Cited

U.S. PATENT DOCUMENTS

| | | | |
|---|---|---|---|
| 3,596,545 | A | 8/1971 | Eisenhardt |
| 3,790,744 | A | 2/1974 | Bowen |
| 4,030,503 | A | 6/1977 | Clark, III |
| 4,334,535 | A | 6/1982 | Wilson et al. |
| 4,560,378 | A | 12/1985 | Weiland |
| 4,585,436 | A | 4/1986 | Davis et al. |
| 4,778,559 | A | 10/1988 | McNeilly |
| 4,964,320 | A | 10/1990 | Lee, Jr. |
| 4,989,606 | A | 2/1991 | Gehrich et al. |
| 5,073,694 | A | 12/1991 | Tessier et al. |
| 5,108,419 | A | 4/1992 | Reger et al. |
| 5,160,342 | A | 11/1992 | Reger et al. |
| 5,171,383 | A | 12/1992 | Sagae et al. |
| 5,195,408 | A | 3/1993 | Niehaus |
| 5,211,183 | A | 5/1993 | Wilson |
| 5,234,451 | A | 8/1993 | Osypka |
| 5,265,622 | A | 11/1993 | Barbere |
| 5,324,276 | A | 6/1994 | Rosenberg |
| 5,370,609 | A | 12/1994 | Drasler et al. |
| 5,378,234 | A | 1/1995 | Hammerslag et al. |
| 5,383,387 | A | 1/1995 | Chesterfield et al. |
| 5,398,568 | A | 3/1995 | Worrell et al. |
| 5,423,849 | A | 6/1995 | Engelson et al. |
| 5,449,372 | A | 9/1995 | Schmaltz et al. |
| 5,484,409 | A | 1/1996 | Atkinson et al. |
| 5,522,822 | A | 6/1996 | Phelps et al. |
| 5,537,696 | A | 7/1996 | Chartier |
| 5,562,641 | A | 10/1996 | Flomenblit et al. |
| 5,573,520 | A | 11/1996 | Schwartz |
| 5,578,074 | A | 11/1996 | Mirigian |
| 5,624,508 | A | 4/1997 | Flomenblit et al. |
| 5,645,558 | A | 7/1997 | Horton |
| 5,690,120 | A | 11/1997 | Jacobsen |
| 5,695,506 | A | 12/1997 | Pike et al. |
| 5,695,507 | A | 12/1997 | Auth et al. |
| 5,697,899 | A | 12/1997 | Hillman et al. |
| 5,725,570 | A | 3/1998 | Heath |
| 5,725,572 | A | 3/1998 | Lam et al. |
| 5,733,400 | A | 3/1998 | Gore et al. |
| 5,741,429 | A | 4/1998 | Donadio, III et al. |
| 5,766,219 | A | 6/1998 | Horton |
| 5,780,807 | A | 7/1998 | Saunders |
| 5,836,066 | A | 11/1998 | Ingram |
| 5,843,051 | A | 12/1998 | Adams et al. |
| 5,843,117 | A | 12/1998 | Alt et al. |
| 5,849,037 | A | 12/1998 | Frid |
| 5,865,816 | A | 2/1999 | Quinn |
| 5,868,708 | A | 2/1999 | Hart et al. |
| 5,876,568 | A | 3/1999 | Kindersley |
| 5,879,499 | A | 3/1999 | Corvi |
| 5,882,444 | A | 3/1999 | Flomenblit et al. |
| 5,895,398 | A | 4/1999 | Wensel et al. |
| 5,895,407 | A | 4/1999 | Jayaraman |
| 5,897,567 | A | 4/1999 | Ressemann et al. |
| 5,911,731 | A | 6/1999 | Pham et al. |
| 5,941,869 | A | 8/1999 | Patterson et al. |
| 5,944,701 | A | 8/1999 | Dubrul |
| 5,951,599 | A | 9/1999 | McCrory |
| 5,972,019 | A | 10/1999 | Engelson et al. |
| 5,994,667 | A | 11/1999 | Merdan et al. |
| 5,996,929 | A | 12/1999 | Mazodier et al. |
| 6,019,778 | A | 2/2000 | Wilson et al. |
| 6,027,863 | A | 2/2000 | Donadio, III |
| 6,030,406 | A | 2/2000 | Davis et al. |
| 6,030,586 | A | 2/2000 | Kuan |
| 6,066,149 | A | 5/2000 | Samson et al. |
| 6,080,170 | A | 6/2000 | Nash et al. |
| 6,090,118 | A | 7/2000 | McGuckin, Jr. |
| 6,102,890 | A | 8/2000 | Stivland et al. |
| 6,102,933 | A | 8/2000 | Lee et al. |
| 6,107,004 | A | 8/2000 | Donadio, III |
| 6,114,653 | A | 9/2000 | Gustafson |
| 6,146,370 | A | 11/2000 | Barbut |
| 6,146,396 | A | 11/2000 | Konya et al. |
| 6,149,682 | A | 11/2000 | Frid |
| 6,165,199 | A | 12/2000 | Barbut |
| 6,165,292 | A | 12/2000 | Abrams et al. |
| 6,168,622 | B1 | 1/2001 | Mazzocchi |
| 6,174,330 | B1 | 1/2001 | Stinson |
| 6,203,561 | B1 | 3/2001 | Ramee et al. |
| 6,227,436 | B1 | 5/2001 | Nishikawa et al. |
| 6,237,460 | B1 | 5/2001 | Frid |
| 6,241,691 | B1 | 6/2001 | Ferrera et al. |
| 6,254,633 | B1 | 7/2001 | Pinchuk et al. |
| 6,258,115 | B1 | 7/2001 | Dubrul |
| 6,262,390 | B1 | 7/2001 | Goland |
| 6,281,262 | B1 | 8/2001 | Shikinami |
| 6,290,721 | B1 | 9/2001 | Heath |
| 6,346,117 | B1 | 2/2002 | Greenhalgh |
| 6,348,063 | B1 | 2/2002 | Yassour et al. |
| 6,350,271 | B1 | 2/2002 | Kurz et al. |
| 6,369,355 | B1 | 4/2002 | Saunders |
| 6,375,668 | B1 | 4/2002 | Gifford et al. |
| 6,383,204 | B1 | 5/2002 | Ferrera |
| 6,383,205 | B1 | 5/2002 | Samson et al. |
| 6,391,044 | B1 | 5/2002 | Yadav et al. |
| 6,395,014 | B1 | 5/2002 | Macoviak et al. |
| 6,428,558 | B1 | 8/2002 | Jones et al. |
| 6,447,531 | B1 | 9/2002 | Amplatz |
| 6,482,217 | B1 | 11/2002 | Pintor et al. |
| 6,506,204 | B2 | 1/2003 | Mazzocchi |
| 6,511,492 | B1 | 1/2003 | Rosenbluth et al. |
| 6,511,504 | B1 | 1/2003 | Lau et al. |
| 6,514,273 | B1 | 2/2003 | Voss et al. |
| 6,517,888 | B1 | 2/2003 | Weber |
| 6,530,935 | B2 | 3/2003 | Wensel et al. |
| 6,530,939 | B1 | 3/2003 | Hopkins et al. |
| 6,540,722 | B1 | 4/2003 | Boyle et al. |
| 6,544,276 | B1 | 4/2003 | Azizi |
| 6,544,279 | B1 | 4/2003 | Hopkins et al. |
| 6,554,848 | B2 | 4/2003 | Boylan et al. |
| 6,563,080 | B2 | 5/2003 | Shapovalov et al. |
| 6,569,183 | B1 | 5/2003 | Kim et al. |
| 6,585,755 | B2 | 7/2003 | Jackson et al. |
| 6,589,263 | B1 | 7/2003 | Hopkins et al. |
| 6,589,265 | B1 | 7/2003 | Palmer et al. |
| 6,602,264 | B1 | 8/2003 | McGuckin, Jr. |
| 6,605,111 | B2 | 8/2003 | Bose et al. |
| 6,610,077 | B1 | 8/2003 | Hancock et al. |
| 6,612,012 | B2 | 9/2003 | Mitelberg et al. |
| 6,626,936 | B2 | 9/2003 | Stinson |
| 6,635,070 | B2 | 10/2003 | Leeflang et al. |
| 6,652,576 | B1 | 11/2003 | Stalker |
| 6,666,882 | B1 | 12/2003 | Bose et al. |
| 6,669,721 | B1 | 12/2003 | Bose et al. |
| 6,673,089 | B1 | 1/2004 | Yassour et al. |
| 6,679,893 | B1 | 1/2004 | Tran |
| 6,682,546 | B2 | 1/2004 | Amplatz |
| 6,689,986 | B2 | 2/2004 | Patel et al. |
| 6,692,504 | B2 | 2/2004 | Kurz et al. |
| 6,695,813 | B1 | 2/2004 | Boyle et al. |
| 6,696,666 | B2 | 2/2004 | Merdan et al. |
| 6,696,667 | B1 | 2/2004 | Flanagan |
| 6,710,285 | B2 | 3/2004 | Brown et al. |
| 6,719,934 | B2 | 4/2004 | Stinson |
| 6,740,112 | B2 | 5/2004 | Yodfat et al. |
| 6,749,560 | B1 | 6/2004 | Konstorum et al. |
| 6,749,619 | B2 | 6/2004 | Ouriel et al. |
| 6,773,448 | B2 | 8/2004 | Kusleika et al. |
| 6,777,647 | B1 | 8/2004 | Messal et al. |
| 6,818,063 | B1 | 11/2004 | Kerrigan |
| 6,837,901 | B2 | 1/2005 | Rabkin et al. |
| 6,840,950 | B2 | 1/2005 | Stanford et al. |
| 6,844,603 | B2 | 1/2005 | Georgakos et al. |

(56) References Cited

U.S. PATENT DOCUMENTS

| | | | |
|---|---|---|---|
| 6,849,081 | B2 | 2/2005 | Sepetka et al. |
| 6,855,153 | B2 | 2/2005 | Saadat |
| 6,855,909 | B2 | 2/2005 | Patel et al. |
| 6,860,893 | B2 | 3/2005 | Wallace et al. |
| 6,861,615 | B2 | 3/2005 | Wojcik et al. |
| 6,862,794 | B2 | 3/2005 | Hopkins |
| 6,867,389 | B2 | 3/2005 | Shapovalov et al. |
| 6,920,677 | B2 | 7/2005 | Dolan et al. |
| 6,927,359 | B2 | 8/2005 | Kleine et al. |
| 6,953,472 | B2 | 10/2005 | Palmer et al. |
| 6,964,670 | B1 | 11/2005 | Shah et al. |
| 6,977,355 | B2 | 12/2005 | Duley et al. |
| 7,004,954 | B1 | 2/2006 | Voss et al. |
| 7,029,494 | B2 | 4/2006 | Soun et al. |
| 7,038,334 | B2 | 5/2006 | Botos et al. |
| 7,083,640 | B2 | 8/2006 | Lombardi et al. |
| 7,093,416 | B2 | 8/2006 | Johnson et al. |
| 7,093,527 | B2 | 8/2006 | Rapaport et al. |
| 7,105,003 | B2 | 9/2006 | Hiltebrandt |
| 7,128,073 | B1 | 10/2006 | van der Burg et al. |
| 7,128,752 | B2 | 10/2006 | Bales |
| 7,131,986 | B2 | 11/2006 | Sirhan et al. |
| 7,152,605 | B2 | 12/2006 | Khairkhahan et al. |
| 7,172,614 | B2 | 2/2007 | Boyle et al. |
| 7,179,273 | B1 | 2/2007 | Palmer et al. |
| 7,211,109 | B2 | 5/2007 | Thompson |
| 7,252,680 | B2 | 8/2007 | Freitag |
| 7,300,429 | B2 | 11/2007 | Fitzgerald et al. |
| 7,306,618 | B2 | 12/2007 | Demond et al. |
| 7,306,624 | B2 | 12/2007 | Yodfat et al. |
| 7,344,546 | B2 | 3/2008 | Wulfman et al. |
| 7,374,564 | B2 | 5/2008 | Brown |
| 7,381,198 | B2 | 6/2008 | Noriega et al. |
| 7,410,491 | B2 | 8/2008 | Hopkins et al. |
| 7,410,602 | B2 | 8/2008 | Davey et al. |
| 7,462,192 | B2 | 12/2008 | Norton et al. |
| 7,476,034 | B2 | 1/2009 | Shedlov et al. |
| 7,572,290 | B2 | 8/2009 | Yodfat et al. |
| 7,582,101 | B2 | 9/2009 | Jones et al. |
| 7,588,597 | B2 | 9/2009 | Frid |
| 7,618,434 | B2 | 11/2009 | Santra et al. |
| 7,621,870 | B2 | 11/2009 | Berrada et al. |
| 7,622,070 | B2 | 11/2009 | Atladottir et al. |
| 7,651,514 | B2 | 1/2010 | Salahieh et al. |
| 7,735,493 | B2 | 6/2010 | van der Burg et al. |
| 7,763,011 | B2 | 7/2010 | Ortiz et al. |
| 7,780,646 | B2 | 8/2010 | Farnholtz |
| 7,786,406 | B2 | 8/2010 | Flanagan |
| 7,828,790 | B2 | 11/2010 | Griffin |
| 7,837,726 | B2 | 11/2010 | Von Oepen et al. |
| 7,857,844 | B2 | 12/2010 | Norton et al. |
| 7,875,050 | B2 | 1/2011 | Samson et al. |
| 7,879,062 | B2 | 2/2011 | Galdonik et al. |
| 7,892,188 | B2 | 2/2011 | Walker et al. |
| 7,922,732 | B2 | 4/2011 | Mazzocchi et al. |
| 7,932,479 | B2 | 4/2011 | Bialas et al. |
| 7,942,925 | B2 | 5/2011 | Yodfat et al. |
| 7,955,345 | B2 | 6/2011 | Kucharczyk et al. |
| 7,955,449 | B2 | 6/2011 | Prokoshkin et al. |
| 7,971,333 | B2 | 7/2011 | Gale et al. |
| 7,989,042 | B2 | 8/2011 | Obara et al. |
| 8,003,157 | B2 | 8/2011 | Andreacchi et al. |
| 8,043,326 | B2 | 10/2011 | Hancock et al. |
| 8,044,322 | B2 | 10/2011 | Merdan |
| 8,052,640 | B2 | 11/2011 | Fiorella et al. |
| 8,088,140 | B2 | 1/2012 | Ferrera et al. |
| 8,092,483 | B2 | 1/2012 | Galdonik et al. |
| 8,092,486 | B2 | 1/2012 | Berrada et al. |
| 8,092,508 | B2 | 1/2012 | Leynov et al. |
| 8,142,456 | B2 | 3/2012 | Rosqueta et al. |
| 8,147,534 | B2 | 4/2012 | Berez et al. |
| 8,152,833 | B2 | 4/2012 | Zaver et al. |
| 8,157,833 | B2 | 4/2012 | Au et al. |
| 8,192,484 | B2 | 6/2012 | Frid |
| 8,217,303 | B2 | 7/2012 | Baxter et al. |
| 8,236,042 | B2 | 8/2012 | Berez et al. |
| 8,257,421 | B2 | 9/2012 | Berez et al. |
| 8,261,648 | B1 | 9/2012 | Marchand et al. |
| 8,267,985 | B2 | 9/2012 | Garcia et al. |
| 8,267,986 | B2 | 9/2012 | Berez et al. |
| 8,273,101 | B2 | 9/2012 | Garcia et al. |
| 8,278,593 | B2 | 10/2012 | Bialas et al. |
| 8,308,712 | B2 | 11/2012 | Provost et al. |
| RE43,882 | E | 12/2012 | Hopkins et al. |
| 8,333,796 | B2 | 12/2012 | Tompkins et al. |
| 8,333,897 | B2 | 12/2012 | Bialas et al. |
| 8,361,095 | B2 | 1/2013 | Osborne |
| 8,361,138 | B2 | 1/2013 | Adams |
| 8,394,119 | B2 | 3/2013 | Zaver et al. |
| 8,398,670 | B2 | 3/2013 | Amplatz et al. |
| 8,398,701 | B2 | 3/2013 | Berez et al. |
| 8,409,267 | B2 | 4/2013 | Berez et al. |
| 8,409,269 | B2 | 4/2013 | Berez et al. |
| 8,409,270 | B2 | 4/2013 | Clerc et al. |
| 8,419,658 | B2 | 4/2013 | Eskuri |
| 8,419,787 | B2 | 4/2013 | Yodfat et al. |
| 8,444,668 | B2 | 5/2013 | Jones et al. |
| 8,500,788 | B2 | 8/2013 | Berez et al. |
| 8,529,614 | B2 | 9/2013 | Berez et al. |
| 8,617,234 | B2 | 12/2013 | Garcia et al. |
| 8,623,067 | B2 | 1/2014 | Berez et al. |
| 8,623,071 | B2 | 1/2014 | Lundkvist et al. |
| 8,628,564 | B2 | 1/2014 | Berez et al. |
| 8,679,150 | B1 | 3/2014 | Janardhan et al. |
| 8,690,907 | B1 | 4/2014 | Janardhan et al. |
| 8,715,314 | B1 | 5/2014 | Janardhan et al. |
| 8,715,315 | B1 | 5/2014 | Janardhan et al. |
| 8,715,316 | B1 | 5/2014 | Janardhan et al. |
| 8,715,317 | B1 | 5/2014 | Janardhan et al. |
| 8,721,676 | B1 | 5/2014 | Janardhan et al. |
| 8,721,677 | B1 | 5/2014 | Janardhan et al. |
| 8,728,116 | B1 | 5/2014 | Janardhan et al. |
| 8,728,117 | B1 | 5/2014 | Janardhan et al. |
| 8,733,618 | B1 | 5/2014 | Janardhan et al. |
| 8,735,777 | B1 | 5/2014 | Janardhan et al. |
| 8,747,432 | B1 | 6/2014 | Janardhan et al. |
| 8,753,371 | B1 | 6/2014 | Janardhan et al. |
| 8,783,151 | B1 | 7/2014 | Janardhan et al. |
| 8,784,446 | B1 | 7/2014 | Janardhan et al. |
| 8,789,452 | B1 | 7/2014 | Janardhan et al. |
| 8,790,365 | B1 | 7/2014 | Janardhan et al. |
| 8,795,330 | B1 | 8/2014 | Janardhan et al. |
| 8,803,030 | B1 | 8/2014 | Janardhan et al. |
| 8,813,625 | B1 | 8/2014 | Janardhan et al. |
| 8,816,247 | B1 | 8/2014 | Janardhan et al. |
| 8,828,045 | B1 | 9/2014 | Janardhan et al. |
| 8,845,678 | B1 | 9/2014 | Janardhan et al. |
| 8,845,679 | B1 | 9/2014 | Janardhan et al. |
| 8,852,227 | B1 | 10/2014 | Janardhan et al. |
| 8,859,934 | B1 | 10/2014 | Janardhan et al. |
| 8,863,631 | B1 | 10/2014 | Janardhan et al. |
| 8,866,049 | B1 | 10/2014 | Janardhan et al. |
| 8,869,670 | B1 | 10/2014 | Janardhan et al. |
| 8,870,901 | B1 | 10/2014 | Janardhan et al. |
| 8,870,910 | B1 | 10/2014 | Janardhan et al. |
| 8,872,068 | B1 | 10/2014 | Janardhan et al. |
| 8,874,434 | B2 | 10/2014 | Collobert et al. |
| 8,882,797 | B2 | 11/2014 | Janardhan et al. |
| 8,895,891 | B2 | 11/2014 | Janardhan et al. |
| 8,904,914 | B2 | 12/2014 | Janardhan et al. |
| 8,910,555 | B2 | 12/2014 | Janardhan et al. |
| 2001/0031980 | A1 | 10/2001 | Wensel et al. |
| 2002/0010487 | A1 | 1/2002 | Evans et al. |
| 2002/0052638 | A1 | 5/2002 | Zadno-Azizi |
| 2002/0082558 | A1 | 6/2002 | Samson et al. |
| 2002/0091355 | A1 | 7/2002 | Hayden |
| 2002/0099436 | A1 | 7/2002 | Thornton et al. |
| 2002/0111648 | A1 | 8/2002 | Kusleika et al. |
| 2002/0133111 | A1 | 9/2002 | Shadduck |
| 2002/0143349 | A1 | 10/2002 | Gifford, III et al. |
| 2002/0188314 | A1 | 12/2002 | Anderson et al. |
| 2002/0193866 | A1 | 12/2002 | Saunders |
| 2002/0194670 | A1 | 12/2002 | Hashemi |
| 2002/0198550 | A1 | 12/2002 | Nash et al. |

(56) References Cited

U.S. PATENT DOCUMENTS

| | | |
|---|---|---|
| 2002/0198589 A1 | 12/2002 | Leong |
| 2003/0004537 A1 | 1/2003 | Boyle et al. |
| 2003/0065356 A1 | 4/2003 | Tsugita et al. |
| 2003/0097094 A1 | 5/2003 | Ouriel et al. |
| 2003/0097710 A1 | 5/2003 | Adrian |
| 2003/0100945 A1 | 5/2003 | Yodfat et al. |
| 2003/0114919 A1 | 6/2003 | McQuiston et al. |
| 2003/0135265 A1 | 7/2003 | Stinson |
| 2003/0176884 A1 | 9/2003 | Berrada et al. |
| 2003/0225448 A1 | 12/2003 | Gerberding |
| 2003/0226833 A1 | 12/2003 | Shapovalov et al. |
| 2004/0004061 A1 | 1/2004 | Merdan |
| 2004/0004063 A1 | 1/2004 | Merdan |
| 2004/0024416 A1 | 2/2004 | Yodfat et al. |
| 2004/0044391 A1 | 3/2004 | Porter |
| 2004/0073293 A1 | 4/2004 | Thompson |
| 2004/0073300 A1 | 4/2004 | Chouinard et al. |
| 2004/0088037 A1 | 5/2004 | Machreiner et al. |
| 2004/0089643 A1 | 5/2004 | Jones et al. |
| 2004/0093015 A1 | 5/2004 | Ogle |
| 2004/0098023 A1 | 5/2004 | Lee et al. |
| 2004/0098033 A1 | 5/2004 | Leeflang et al. |
| 2004/0118902 A1 | 6/2004 | Adams |
| 2004/0167613 A1 | 8/2004 | Yodfat et al. |
| 2004/0168298 A1 | 9/2004 | Dolan et al. |
| 2004/0182451 A1 | 9/2004 | Poirier |
| 2004/0193140 A1 | 9/2004 | Griffin et al. |
| 2004/0204737 A1 | 10/2004 | Boismier et al. |
| 2004/0220610 A1 | 11/2004 | Kreidler et al. |
| 2004/0225186 A1 | 11/2004 | Horne, Jr. et al. |
| 2004/0236412 A1 | 11/2004 | Brar et al. |
| 2005/0015110 A1 | 1/2005 | Fogarty et al. |
| 2005/0021075 A1 | 1/2005 | Bonnette et al. |
| 2005/0035101 A1 | 2/2005 | Jones et al. |
| 2005/0050624 A1 | 3/2005 | Pangramuyen |
| 2005/0120471 A1 | 6/2005 | Lim |
| 2005/0131522 A1 | 6/2005 | Stinson et al. |
| 2005/0133486 A1 | 6/2005 | Baker et al. |
| 2005/0149108 A1 | 7/2005 | Cox |
| 2005/0192624 A1 | 9/2005 | Mazzocchi et al. |
| 2005/0203553 A1 | 9/2005 | Maschke |
| 2005/0228417 A1 | 10/2005 | Teitelbaum et al. |
| 2005/0234474 A1 | 10/2005 | DeMello et al. |
| 2005/0236911 A1 | 10/2005 | Botos et al. |
| 2005/0251200 A1 | 11/2005 | Porter |
| 2005/0256563 A1 | 11/2005 | Clerc et al. |
| 2005/0267510 A1 | 12/2005 | Razack |
| 2005/0277975 A1 | 12/2005 | Saadat et al. |
| 2005/0283186 A1 | 12/2005 | Berrada et al. |
| 2006/0004346 A1 | 1/2006 | Begg |
| 2006/0009799 A1 | 1/2006 | Kleshinski et al. |
| 2006/0020286 A1 | 1/2006 | Niermann |
| 2006/0030878 A1 | 2/2006 | Anderson et al. |
| 2006/0047286 A1 | 3/2006 | West |
| 2006/0070516 A1 | 4/2006 | McCullagh et al. |
| 2006/0100687 A1 | 5/2006 | Fahey et al. |
| 2006/0116712 A1 | 6/2006 | Sepetka et al. |
| 2006/0116713 A1 | 6/2006 | Sepetka et al. |
| 2006/0122687 A1 | 6/2006 | Bassler et al. |
| 2006/0136043 A1 | 6/2006 | Cully et al. |
| 2006/0161198 A1 | 7/2006 | Sakai et al. |
| 2006/0161253 A1 | 7/2006 | Lesh |
| 2006/0206196 A1 | 9/2006 | Porter |
| 2006/0206200 A1 | 9/2006 | Garcia et al. |
| 2006/0229638 A1 | 10/2006 | Abrams et al. |
| 2006/0229645 A1 | 10/2006 | Bonnette et al. |
| 2006/0241739 A1 | 10/2006 | Besselink et al. |
| 2006/0264904 A1 | 11/2006 | Kerby et al. |
| 2006/0276887 A1 | 12/2006 | Brady et al. |
| 2007/0016233 A1 | 1/2007 | Ferrera et al. |
| 2007/0027522 A1 | 2/2007 | Chang et al. |
| 2007/0034615 A1 | 2/2007 | Kleine |
| 2007/0045255 A1 | 3/2007 | Kleine et al. |
| 2007/0060880 A1 | 3/2007 | Gregorich et al. |
| 2007/0060942 A2 | 3/2007 | Zadno-Azizi |
| 2007/0112381 A1 | 5/2007 | Figulla et al. |
| 2007/0118165 A1 | 5/2007 | DeMello et al. |
| 2007/0135832 A1 | 6/2007 | Wholey et al. |
| 2007/0135833 A1 | 6/2007 | Talpade et al. |
| 2007/0142903 A1 | 6/2007 | Dave |
| 2007/0168019 A1 | 7/2007 | Amplatz et al. |
| 2007/0173921 A1 | 7/2007 | Wholey et al. |
| 2007/0185500 A1 | 8/2007 | Martin et al. |
| 2007/0185501 A1 | 8/2007 | Martin et al. |
| 2007/0197103 A1 | 8/2007 | Martin et al. |
| 2007/0198029 A1 | 8/2007 | Martin et al. |
| 2007/0198030 A1 | 8/2007 | Martin et al. |
| 2007/0225749 A1 | 9/2007 | Martin et al. |
| 2007/0228023 A1 | 10/2007 | Kleine et al. |
| 2007/0233174 A1 | 10/2007 | Hocking et al. |
| 2007/0265656 A1 | 11/2007 | Amplatz et al. |
| 2007/0288054 A1 | 12/2007 | Tanaka et al. |
| 2008/0027356 A1 | 1/2008 | Chen et al. |
| 2008/0033475 A1 | 2/2008 | Meng |
| 2008/0065008 A1 | 3/2008 | Barbut et al. |
| 2008/0077119 A1 | 3/2008 | Snyder et al. |
| 2008/0097393 A1 | 4/2008 | Chen |
| 2008/0097395 A1 | 4/2008 | Adams et al. |
| 2008/0097398 A1 | 4/2008 | Mitelberg et al. |
| 2008/0107641 A1 | 5/2008 | Kuebler |
| 2008/0195230 A1 | 8/2008 | Quijano et al. |
| 2008/0221601 A1 | 9/2008 | Huynh et al. |
| 2008/0228209 A1 | 9/2008 | DeMello et al. |
| 2008/0234722 A1 | 9/2008 | Bonnette et al. |
| 2008/0262487 A1 | 10/2008 | Wensel et al. |
| 2008/0269774 A1 | 10/2008 | Garcia et al. |
| 2008/0275464 A1 | 11/2008 | Abrams et al. |
| 2008/0294181 A1 | 11/2008 | Wensel et al. |
| 2008/0296274 A1 | 12/2008 | Bialas et al. |
| 2008/0300673 A1 | 12/2008 | Clerc et al. |
| 2008/0306499 A1 | 12/2008 | Katoh et al. |
| 2008/0312681 A1 | 12/2008 | Ansel et al. |
| 2009/0025820 A1 | 1/2009 | Adams |
| 2009/0043283 A1 | 2/2009 | Turnlund et al. |
| 2009/0062841 A1 | 3/2009 | Amplatz et al. |
| 2009/0076540 A1 | 3/2009 | Marks et al. |
| 2009/0082800 A1 | 3/2009 | Janardhan |
| 2009/0099647 A1 | 4/2009 | Glimsdale et al. |
| 2009/0105737 A1 | 4/2009 | Fulkerson et al. |
| 2009/0105753 A1 | 4/2009 | Greenhalgh et al. |
| 2009/0112251 A1 | 4/2009 | Qian et al. |
| 2009/0114626 A1 | 5/2009 | Oberg |
| 2009/0125097 A1 | 5/2009 | Bruszewski et al. |
| 2009/0157048 A1 | 6/2009 | Sutermeister et al. |
| 2009/0172935 A1 | 7/2009 | Anderson et al. |
| 2009/0188269 A1 | 7/2009 | Attarwala et al. |
| 2009/0198269 A1 | 8/2009 | Hannes et al. |
| 2009/0209855 A1 | 8/2009 | Drilling et al. |
| 2009/0221995 A1 | 9/2009 | Harlan |
| 2009/0248071 A1 | 10/2009 | Saint et al. |
| 2009/0264985 A1 | 10/2009 | Bruszewski |
| 2009/0275974 A1 | 11/2009 | Marchand et al. |
| 2009/0287120 A1 | 11/2009 | Ferren et al. |
| 2009/0297582 A1 | 12/2009 | Meyer et al. |
| 2009/0306702 A1 | 12/2009 | Miloslavski et al. |
| 2009/0306762 A1 | 12/2009 | McCullagh et al. |
| 2009/0312834 A1 | 12/2009 | Wood et al. |
| 2009/0318892 A1 | 12/2009 | Aboytes et al. |
| 2010/0010622 A1 | 1/2010 | Lowe et al. |
| 2010/0023034 A1 | 1/2010 | Linder et al. |
| 2010/0023105 A1 | 1/2010 | Levy et al. |
| 2010/0030256 A1 | 2/2010 | Dubrul et al. |
| 2010/0049240 A1 | 2/2010 | Papp |
| 2010/0069882 A1 | 3/2010 | Jennings et al. |
| 2010/0069948 A1 | 3/2010 | Veznedaroglu et al. |
| 2010/0102046 A1 | 4/2010 | Huang et al. |
| 2010/0114017 A1 | 5/2010 | Lenker et al. |
| 2010/0131000 A1 | 5/2010 | DeMello et al. |
| 2010/0152834 A1 | 6/2010 | Hannes et al. |
| 2010/0191319 A1 | 7/2010 | Lilburn et al. |
| 2010/0193485 A1 | 8/2010 | Anukhin et al. |
| 2010/0217276 A1 | 8/2010 | Garrison et al. |
| 2010/0217303 A1 | 8/2010 | Goodwin |
| 2010/0230391 A1 | 9/2010 | Baxter et al. |

(56) References Cited

U.S. PATENT DOCUMENTS

| | | |
|---|---|---|
| 2010/0262221 A1 | 10/2010 | Schafer et al. |
| 2010/0280592 A1 | 11/2010 | Shin et al. |
| 2010/0318097 A1 | 12/2010 | Ferrera et al. |
| 2011/0036820 A1 | 2/2011 | Merdan |
| 2011/0046719 A1 | 2/2011 | Frid |
| 2011/0056350 A1 | 3/2011 | Gale et al. |
| 2011/0060359 A1 | 3/2011 | Hannes et al. |
| 2011/0060400 A1 | 3/2011 | Oepen et al. |
| 2011/0077620 A1 | 3/2011 | deBeer |
| 2011/0082493 A1 | 4/2011 | Samson et al. |
| 2011/0087147 A1 | 4/2011 | Garrison et al. |
| 2011/0094708 A1 | 4/2011 | Cardone |
| 2011/0125132 A1 | 5/2011 | Krolik et al. |
| 2011/0125181 A1 | 5/2011 | Brady et al. |
| 2011/0152993 A1 | 6/2011 | Marchand et al. |
| 2011/0160757 A1 | 6/2011 | Ferrera et al. |
| 2011/0160760 A1 | 6/2011 | Ferrera et al. |
| 2011/0160761 A1 | 6/2011 | Ferrera et al. |
| 2011/0190797 A1 | 8/2011 | Fulkerson et al. |
| 2011/0190868 A1 | 8/2011 | Ducke et al. |
| 2011/0203446 A1 | 8/2011 | Dow et al. |
| 2011/0208227 A1 | 8/2011 | Becking |
| 2011/0210108 A1 | 9/2011 | Bialas et al. |
| 2011/0213403 A1 | 9/2011 | Aboytes |
| 2011/0238041 A1 | 9/2011 | Lim et al. |
| 2011/0264133 A1 | 10/2011 | Hanlon et al. |
| 2011/0265943 A1 | 11/2011 | Rosqueta et al. |
| 2011/0283871 A1 | 11/2011 | Adams |
| 2011/0295359 A1 | 12/2011 | Clerc et al. |
| 2011/0307072 A1 | 12/2011 | Anderson et al. |
| 2012/0022579 A1 | 1/2012 | Fulton |
| 2012/0029616 A1 | 2/2012 | Guerriero et al. |
| 2012/0055614 A1 | 3/2012 | Hancock et al. |
| 2012/0057813 A1 | 3/2012 | Von Oepen |
| 2012/0065660 A1 | 3/2012 | Ferrera et al. |
| 2012/0083824 A1 | 4/2012 | Berrada et al. |
| 2012/0116443 A1 | 5/2012 | Ferrera et al. |
| 2012/0158124 A1 | 6/2012 | Zaver et al. |
| 2012/0164157 A1 | 6/2012 | Kuebler |
| 2012/0179192 A1 | 7/2012 | Fogarty et al. |
| 2012/0197283 A1 | 8/2012 | Marchand et al. |
| 2012/0209312 A1 | 8/2012 | Aggerholm et al. |
| 2012/0231414 A1 | 9/2012 | Johnson |
| 2012/0232655 A1 | 9/2012 | Lorrison et al. |
| 2012/0239066 A1 | 9/2012 | Levine et al. |
| 2012/0239074 A1 | 9/2012 | Aboytes et al. |
| 2012/0245517 A1 | 9/2012 | Tegels |
| 2012/0259404 A1 | 10/2012 | Tieu et al. |
| 2012/0265238 A1 | 10/2012 | Hopkins et al. |
| 2012/0271337 A1 | 10/2012 | Figulla et al. |
| 2012/0271403 A1 | 10/2012 | Gries |
| 2012/0273467 A1 | 11/2012 | Baxter et al. |
| 2012/0277850 A1 | 11/2012 | Bertini |
| 2012/0283768 A1 | 11/2012 | Cox et al. |
| 2012/0290067 A1 | 11/2012 | Cam et al. |
| 2012/0316598 A1 | 12/2012 | Becking et al. |
| 2012/0330347 A1 | 12/2012 | Becking et al. |
| 2013/0030460 A1 | 1/2013 | Marks et al. |
| 2013/0060323 A1 | 3/2013 | McHugo |
| 2013/0066357 A1 | 3/2013 | Aboytes et al. |
| 2013/0085515 A1 | 4/2013 | To et al. |
| 2013/0092298 A1 | 4/2013 | Bregulla et al. |
| 2013/0096587 A1 | 4/2013 | Smith et al. |
| 2013/0167960 A1 | 7/2013 | Pethe et al. |
| 2013/0220610 A1 | 8/2013 | Mosing et al. |
| 2013/0240096 A1 | 9/2013 | Browne et al. |
| 2013/0327469 A1 | 12/2013 | Pingleton et al. |
| 2014/0128905 A1 | 5/2014 | Molaei |
| 2014/0155908 A1 | 6/2014 | Rosenbluth et al. |
| 2014/0324091 A1 | 10/2014 | Rosenbluth et al. |

FOREIGN PATENT DOCUMENTS

| | | |
|---|---|---|
| EP | 1 904 217 | 3/2013 |
| GB | 667071 | 2/1952 |
| WO | WO 2004/093738 | 11/2004 |
| WO | WO 2007/011353 | 1/2007 |

OTHER PUBLICATIONS

Abbott Laboratories, "Xact Carotid Stent System, RX ACCULINK Carotid Stent System, 2006 Clinical Update for Physicians", 2007.

Adams et al., "Guidelines for the Early Management of Patients with Ischemic Stroke: A Scientific Statement from the Stroke Council of the American Stroke Association," Stroke, 2003, vol. 34, pp. 1056-1083.

Adams et al., "Guidelines for the Early Management of Patients with Ischemic Stroke—2005 Guidelines Update—A Scientific Statement from the Stroke Council of the American Stroke Association," Stroke, 2005, vol. 36, pp. 916-923.

Alligator Retrieval Device Product Brochure, 2009.

Bose et al., "A Novel, Self-Expanding, Nitinol Stent in Medically Refractory Intracranial Atherosclerotic Stenoses, The Wingspan Study," http://stroke.ahajournals.org/, American Heart Association, Inc., 2007, pp. 1531-1537.

Boston Scientific, "Excelsior 1018 Microcatheter, For Peak Performance in GDC Delivery," 2000.

Boston Scientific, "Excelsior 1018 Microcatheter, Neurovascular Access," 2004.

Boston Scientific, "Excelsior SL-10 Microcatheter, Neurovascular Access," 2004.

Boston Scientific, "Excelsior SL-10 Microcatheter, The 10 Microcatheter with a 14 Lumen," 2002.

Boston Scientific, "FilterWire EX, Embolic Protection System, Instruction for Use," Apr. 2004.

Boston Scientific, "Neuroform$^2$ Microdelivery Stent System, Technical Bulletin No. 1—Parent Vessel Protection," 2004.

Boston Scientific, "Neuroform$^2$ Microdelivery Stent System, Neurovascular Reconstruction," 2004.

Boston Scientific, "Neuroform$^3$ Microdelivery Stent System, Confidence Begins with Control," 2005.

Boston Scientific, "Pre-Shaped Microcatheters, Product Selection Guide," 2004.

Boston Scientific, "Renegade 18 Microcatheter, Neurovascular Access," 2004.

Boston Scientific, "Synchro Guidewires, Neurovascular Access," 2004.

Boston Scientific, "Tracker Excel-14 Microcatheter, Engineered for GDC Coil Delivery," 1998.

Boston Scientific, "Tracker Excel-14 Microcatheter, Neurovascular Access," 2004.

Boston Scientific, "Transend Guidewires, Neurovascular Access," 2003.

Braley et al., "Advancements in Braided Materials Technology," 46th Int'l SAMPLE Symposium, May 2001, pp. 2445-2454.

Chestnut Medical Technologies, Inc., "Instructions for Use (IFU), Alligator Retrieval Device (ARD)," 2005.

Concentric Medical, "Instructions for Use, Concentric Micro Catheters", 2003.

Concentric Medical, "Instructions for Use, MERCI retriever X51X6," 2004.

Cordis Corporation, "Cordis CarotidSystem, Cordis Precise Nitinol Self-Expanding Stent and Cordis Angioguard Emboli Capture Guidewire System," 2004.

Cordis Corporation, "Cordis CarotidSystem, Technical Specification and Product Codes," 2006.

Cordis Corporation, "Cordis CarotidSystem RX, Technical Specifications and Product Codes," 2007.

Cordis Endovascular, "Diagnosing Carotid Artery Disease: The Leading Cause of Stroke," Sample News Article #1: "Diagnosis," 2008 or earlier.

Embo Shield, "Xact, Customized for Carotid Arteries, The Barewaire Revolution is Here," 2005.

(56) References Cited

OTHER PUBLICATIONS ev3, "ev3 Carotid Innovations, Redefining Confidence, See what you've been missing . . . ", ev3 The Endovascular Company, 2008 or earlier.

Furlan et al., "Intra-arterial Prourokinase for Acute Ischemic Stroke, The PROCT II Study: A Randomized Controlled Trial," JAMA, Dec. 1, 1999, vol. 282, Issue 21, pp. 2003-2011.

Henkes et al., "A New Device for Endovascular Coil Retrieval from Intracranial Vessels: Alligator Retrieval Device", AJRN Am J. Neuroradiol, Feb. 2006, vol. 27, pp. 327-329.

Micro Therapeutics, Inc., "Mirage .008", Hydrophilic Guidewire, 2000.

Micrus Endovascular, "WATUSI guidewire, Let's Dance," 2006.

Rymer et al., "Organizing regional networks to increase acute stroke intervention", Neurological Research, 2005, vol. 27, Issue 1, pp. S9-S16.

Sarti et al., "International Trends in Mortality From Stroke, 1968 to 1994", http://stroke.ahajournals.org/, American Heart Association, Inc., Apr. 20, 2000, pp. 1588-1601.

University of Minnesota, "Design of Medical Devices Conference," Apr. 17-19, 2007.

Yadav, "Carotid stenting in high-risk patients: Design and rationale of the SAPPHIRE trial", Cleveland Clinic Journal of Medicine, Jan. 2004, vol. 71, Issue 1, pp. S45-S46.

Yadav et al., "Protected Carotid-Artery Stenting versus Endarterectomy in High-Risk Patients," The New England Journal of Medicine, Oct. 7, 2004, vol. 351, Issue 15, pp. 1493-1501 & 1565-1567.

U.S. Appl. No. 60/980,736, filed Oct. 17, 2007.
U.S. Appl. No. 61/044,392, filed Apr. 11, 2008.
U.S. Appl. No. 61/015,154, filed Dec. 19, 2007.
U.S. Appl. No. 60/989,422, filed Nov. 20, 2007.
U.S. Appl. No. 61/019,506, filed Jan. 7, 2008.
U.S. Appl. No. 60/987,384, filed Nov. 12, 2007.
U.S. Appl. No. 61/129,823, filed Jul. 22, 2008.
U.S. Appl. No. 61/202,612, filed Mar. 18, 2009.
US 6,348,062, 02/2002, Hopkins et al. (withdrawn)

SHAPE-SET TEXTILE STRUCTURE BASED MECHANICAL THROMBECTOMY SYSTEMS

CROSS-REFERENCE TO RELATED APPLICATIONS

The present application is a continuation of U.S. patent application Ser. No. 13/952,982, filed Jul. 29, 2013, which claims priority benefit of U.S. Provisional Patent App. No. 61/798,540, filed on Mar. 15, 2013, and the present application claims priority benefit of U.S. Provisional Patent App. No. 61/798,540, filed on Mar. 15, 2013.

Any and all applications for which a foreign or domestic priority claim is identified in the Application Data Sheet as filed with the present application are hereby incorporated by reference under 37 C.F.R. §1.57.

FIELD

The present disclosure generally relates to devices, systems, methods for making, and methods for use in thrombectomy. Several embodiments relate to systems and methods for providing novel approaches for stroke treatment.

BACKGROUND

Stroke is the leading cause of long term disability in the United States and the second leading cause of death worldwide with over 4.4 million deaths in a year (1999). There are over 795,000 new strokes every year in the United States. Around 85% of all strokes are acute ischemic strokes caused from a blockage in a blood vessel or a blood clot occluding a blood vessel. In 1996, the FDA approved a thrombolytic drug to dissolve blood clots called recombinant tissue plasminogen activator (r-tpa). Despite practice guidelines from multiple national organizations stating the intravenous r-tpa is the standard of care for patients with acute ischemic stroke within 3 hours from symptom onset, only 3-4% of patients with acute ischemic stroke received this drug in the United States. Unlike intravenous r-tpa, catheter-based therapies for mechanical thrombectomy can be used for up to 8 hours or beyond from acute ischemic stroke symptom onset and could benefit more people. With advances in regional stroke networks, there are more and more stroke patients who are getting access to intra-arterial thrombolysis and therapies, and are as high as 21.6%.

SUMMARY

Blood clots can range from 5 mm to greater than 55 mm. In addition, blood clots can extend from one vessel diameter to another vessel diameter. There is clearly an unmet need currently for a mechanical thrombectomy device that is gentle and safe on the fragile human blood vessels, that can be customized to the length of the clot or clot burden using the same device by the operator, that can be visualized with ease under X-ray fluoroscopy, that can reach the smallest of human blood vessels, that can be compatible with torsional rasping of the clot, and/or have bonding zones or attachment points that are strong even between dissimilar metals or alloys to avoid the risk of any fracture points, as well as have flexible delivery systems that have good proximal support and good distal flexibility. Several embodiments of the invention provide one or more of the advantages above. In some embodiments, all of the advantages above are provided.

In several embodiments, the device is particularly beneficial because it includes one or more of the following advantages: (i) adapted for and gentle on the fragile blood vessels instead of an expansile laser-cut stent based mechanical thrombectomy device; (ii) tapered to mimic the tapering of the human blood vessels thereby allowing for the use of a single tapered device to remove blood clots extending across different tapering blood vessel diameters; (iii) allows for flexibility during deployment and retrieval in tortuous human blood vessels thereby allowing for longer usable lengths of the device; (iv) comprises a long usable length can be customized to the length of the clot or the clot burden without having to use multiple devices to remove the clot in piece meal; (v) a textile structure based mechanical thrombectomy device allows for torsional rasping of the textile structure around the blood clot to entrap the clot and retrieve it; (vi) allows for filtering distal emboli or debris that may be released; (vii) employs processes to bond the textile structure and the delivery system allow for bonding of dissimilar metals or alloys; (viii) comprises an inlay bonding approach of the textile structure with the delivery system, which allows for a low overall profile and outer diameter of the mechanical thrombectomy device in the collapsed configuration to be less than e.g., 0.0125 inches (0.317 mm); (ix) low overall profile and outer diameter of the mechanical thrombectomy device in the collapsed configuration allows for the device to be deployed with a microcatheter that has an inner lumen diameter of e.g., 0.014 inch or greater (0.355 mm); (x) patterns of radio-opaque filaments or wires to achieve maximal radio-opacity and visibility for the operator during X-ray fluoroscopy; (xi) multiple transition points for the laser-cut delivery system or hypotube, which allows for distal flexibility and proximal support as well as supports the ability to perform torsional rasping of the clot; and/or (xii) the laser-cut hypotube with multiple transition points is incorporated as the core braid for the wall of the microcatheter, which allows for distal flexibility and proximal support for allowing the safe and effective deployment of the textile structure based mechanical thrombectomy device.

Various embodiments of the present invention are shown in the figures and described in detail below.

DRAWINGS

Reference Numerals

Figure 1:
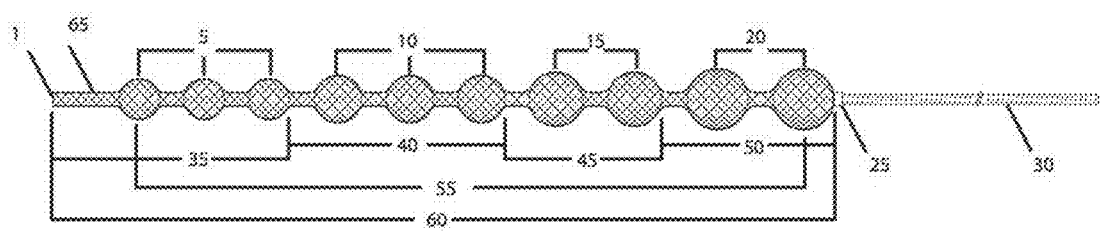
FIG. 1 is a schematic diagram illustrating the 2D view of one of the embodiments with a spherical tapered textile structure.

Part numbers for the Figures are listed below

| Part Number | Description |
| --- | --- |
| 1 | Distal Tip |
| 5 | Extra small spherical bulbs (d = 3 mm) |
| 10 | Small spherical bulbs (d = 3.5 mm) |
| 15 | Medium spherical bulbs (d = 4 mm) |
| 20 | Large spherical bulbs (d = 4.5 mm) |
| 25 | Proximal Marker band |
| 30 | Delivery System/Hypotube |
| 35 | Extra small vessel segment |
| 40 | Small vessel segment |
| 45 | Medium vessel segment |
| 50 | Large vessel segment |
| 55 | Usable length |
| 60 | Proximal marker to distal tip length |
| 65 | Narrow Distal Neck |
| 70 | Wide Distal Neck |
| 75 | Extra Small oblong bulbs |
| 80 | Small oblong bulbs |
| 85 | Medium oblong bulbs |
| 90 | Large oblong bulbs |
| 95 | Narrow neck between bulbs |
| 100 | Non-tapered spherical bulbs (diameter = 1-30 mm) |
| 105 | Non-tapered oblong bulbs (diameter = 1-30 mm) |
| 110 | Proximal neck |
| 115 | Cylindrical shape-set structure |
| 120 | Distal marker band |
| 125 | Distal spherical filter (diameter = 1-30 mm) |
| 130 | Proximal spherical filter (diameter = 1-30 mm) |
| 135 | Distal oblong filter (diameter = 1-30 mm) |
| 140 | Proximal oblong filter (diameter = 1-30 mm) |
| 145 | Yarn Wheel |
| 150 | Spindle |
| 155 | Filament of textile structure |
| 160 | Preform point |
| 165 | Textile structure |
| 170 | Direction of rotation of yarn wheel |
| 175 | Cylindrical mandrel |
| 190 | Laser cut free end of the textile structure |
| 195 | Lead free solder with flux 2 or 3 |
| 200 | Epoxy glue |
| 205 | Any type of bonding agent - solder, epoxy glue etc. |
| 210 | Pinched Ring |
| 215 | Pinched cylinder |
| 220 | Heat Shrink PET tube |
| 225 | Overlay bonding zone |
| 230 | Uncut bonding zone |
| 235 | Hypotube through cross-section of textile structure |
| 240 | Distal to distal overlay bonding zone |
| 245 | Kerf Width |
| 250 | Strut Width |
| 251 | Strut Width 2 |
| 252 | Strut Width 3 |
| 253 | Strut Width 4 |
| 255 | Laser cut length |
| 260 | Anchor point distance (gap between 2 kerfs on same row) |
| 265 | Delivery system wall thickness |
| 270 | Step 1 of diagonal stagger distance between two rows of laser cuts of the same pattern |
| 275 | Step 2 of diagonal stagger distance between two rows of laser cuts of the same pattern |
| 280 | Direction of pattern A laser cut |
| 285 | Direction of pattern B laser cut |
| 295 | Length of delivery system |
| 300 | Inner diameter circumference of delivery system |
| 305 | Outer diameter circumference of delivery system |
| 310 | Direction of folding delivery system (Compressing expanded view into cylindrical view of delivery system) |
| 315 | Inter-pattern stagger distance between rows |
| 320 | Laser cut pattern A |
| 330 | Laser cut pattern A and B interspersed |
| 335 | Rounded kerf edge |
| 340 | Square or sharp kerf edge |
| 345 | wires of delivery system |
| 350 | Bonding zone of textile structure to delivery system |
| 355 | bonding agent for filaments of delivery system |
| 360 | Extra small pitches (Kerf width plus strut width) |
| 365 | Small pitches (Kerf width plus strut width) |
| 370 | Medium pitches (Kerf width plus strut width) |
| 375 | Large pitches (Kerf width plus strut width) |
| 580 | Guide catheter |
| 590 | Microcatheter |
| 600 | Microwire |
| 650 | Blood clot or Clot burden |

DETAILED DESCRIPTION

FIG. 1 is a schematic diagram that illustrates a two-dimensional front view of one of the embodiments with a spherical tapered textile structure. It has three components in one of the embodiments: a shape-set textile structure, a bonding zone at the region of the proximal marker band, and a delivery system or hypotube.

The shape-set tapered textile structure in several embodiments has a distal tip, that in the expanded configuration has an outer diameter of less than e.g., 0.017 inches (0.43 mm) and in the collapsed configuration has an outer diameter of less than e.g., 0.0125 inches (0.317 mm). In several embodiments, the expanded configuration of the tip has a diameter in the range of about 0.35-0.65 mm (e.g., 0.40-0.45 mm). In several embodiments, the collapsed configuration has a diameter in the range of about 0.1-0.34 mm (e.g., 0.25-0.33 mm). In some embodiments, for larger vessels, the expanded configuration has a diameter in the range of about 1-40 mm and a diameter in the range of about 0.5-10 mm in a collapsed configuration. In some embodiments, the ratio of the expanded configuration to the collapsed configuration is 1.2:1-10:1. In several embodiments, the distal neck is narrow and has similar outer diameter in the expanded and collapsed configuration as the distal tip. The distal neck has a length that ranges from about 1-5 mm in one of the embodiments.

In several embodiments, there are a total of 10 spherical bulbs in one of the embodiments with varying diameters in the expanded configuration and in the collapsed configuration has an outer diameter of less than e.g., 0.0125 inches (0.317 mm). In several embodiments, the expanded configuration of the bulbs has a diameter in the range of about 1-6 mm (e.g., 3-4.5 mm). In several embodiments, the collapsed configuration has a diameter in the range of about 0.1-0.9 mm (e.g., 0.25-0.5 mm). In some embodiments, for larger vessels, the expanded configuration has a diameter in the range of about 5-40 mm and a diameter in the range of about 0.5-5 mm in a collapsed configuration. In some embodiments, the ratio of the expanded configuration to the collapsed configuration is 1.2:1-10:1.

In some embodiments, the varying outer diameters of the 10 spherical bulbs in the expanded configuration are as follows in one of the embodiments: The distal three extra-small spherical bulbs have an outer diameter (e.g., d=3 mm) in the expanded configuration and corresponds to the extra-small vessel segments such as the M2 segments of the middle cerebral artery, the next three small spherical bulbs have an outer diameter (e.g., d=3.5 mm) in the expanded configuration and corresponds to the smaller vessel segments such as the distal M1 segment of the middle cerebral artery, the next two medium spherical bulbs have an outer diameter (e.g., d=4 mm) in the expanded configuration and corresponds to the medium vessel segments such as the proximal M1 segment of the middle cerebral artery, and the proximal two large spherical bulbs have an outer diameter (d=4.5 mm) in the expanded configuration that corresponds to the large vessel segments such as the distal supra-clinoid segment of the internal carotid artery. This tapered configuration of the shape-set textile structure allows for adequate and safe deployment of the device across blood vessels with multiple diameters. Although specific diameter numbers are provided in this paragraph, other embodiments include diameters that are +/−5, 10, 15, or 20%.

In some embodiments, 10 bulbs are used. However, in other embodiments, 1-9 bulbs or 11-30 (or more) bulbs may be used. In some embodiments, 5, 6, 7, 8, 9, 10, 11, 12, 13, 14, 15, 16, 17, 18, 19 or 20 bulbs are used. In some conditions, for example in the leg, where clots can be up 20-40 cm, 40-60 bulbs may be used. In some embodiments, 1 bulb is used for every 0.2-5 cm (e.g., about 0.5-2 cm).

In several embodiments, bulbs of various sizes and/or shapes are provided on a single elongate support structure (such as a neck, tube, spindle, spine, rod, backbone, etc.). The elongate support structure may be hollow, filled or partially hollow. The elongate support structure may have a length in the range of about 1-20 cm (e.g., about 4-8 cm, 5-10 cm, etc). In larger vessels (e.g., outside the brain) the length can be about 20-50 cm. The diameter or width of the elongate support structure is in the range of about 0.35-0.65 mm (e.g., 0.40-0.45 mm) in an expanded configuration and in the range of about 0.1-0.34 mm (e.g., 0.25-0.33 mm) in the collapsed configuration. In some embodiments, for larger vessels, the expanded configuration of the elongate support structure has a diameter in the range of about 1-40 mm (e.g., 5-20 mm) and a diameter in the range of about 0.5-10 mm (e.g., 1-2 mm) in a collapsed configuration. Wall thickness of the elongate support structure are, in some embodiments, ranges from about 0.01-4 mm (e.g., about 0.02-1 mm 0.02-0.05 mm, e.g., 0.025 mm). The elongate support structure may be braided, knitted or weaved with two or more strands (e.g., about 12-120 strands, 12-96 strands, 48 strands) in some embodiments. The pattern, in some embodiments, is one-over-one-under-two, one-over-one-under-one, two-over-two-under-two, etc. In some embodiments, the braid angle is in the range of about 45-179 degrees (e.g., about 130-160 degrees, 151 degrees). The picks (or pixels) per inch (PPI) range from about 50-300 PPI (e.g., about 150-190 PPI, e.g., 171 PPI). In some embodiments, increased outward expansile force and/or compression resistance is provided by a higher braid angle and/or higher PPI. In some embodiments, the force/resistance (e.g., radial force) is in a range sufficient to expand a target vessel in the range of about 0%-30%. In some embodiments, the total diameter size of the treatment device is 0.5 mm-1.5 mm greater than the target vessel diameter. In some embodiments, the total diameter size of the treatment device is oversized by 10-50% with respect to the target vessel diameter. The elongate support structure may be made of shape memory alloys (e.g., nickel titanium). In some embodiments, the elongate support structure is about 50-95% (e.g., 75%) nickel titanium and about 5-50% (e.g., 25%) platinum iridium or platinum tungsten or combinations thereof. The radio-opaque portions can be spaced or clustered to increase visibility under x-ray. For example, a thick band pattern may be used which can include 1-12 radio-opaque strands (e.g., filaments, wires, etc.) that are wound adjacently with one another. In several embodiments, the bulbs are integral with the elongate support structure. In other embodiments, the bulbs are coupled (fixably or reversibly coupled) to the elongate support structure.

For example, bulbs size (with respect to the outer diameter in an expanded configuration) is about 0.5-3 mm (e.g., 3 mm), about 3.1-3.9 mm (e.g., 3.5 mm), about 4-4.4 mm (e.g., 4 mm), and about 4.5-7.5 mm (e.g., 4.5 mm) are provided. In some embodiments, the bulbs are sized in the range of about 1 mm-80 mm (e.g., 2 mm-12 mm). Bulbs in range of 4-10 mm may be particular beneficial for larger clots and/or vessels (e.g., in the leg). The sizes above are reduced by 1.3-10 times in the collapsed configuration. In some embodiments, the collapsed configuration of the bulbs is about 50-80% of the inner diameter of the delivery catheter (e.g., microcatheter). In some embodiments, each consecutive bulb is larger than the other. In other embodiments, two sizes are used in an alternate pattern. In yet other embodiments, three or more sizes are used in a series, and each series is repeated two, three, four, five, six, seven, or more times. As an example, if a series of three sizes is alternated, twenty-one bulbs are used. In some embodiments, larger bulbs may be used at the ends, while smaller bulbs are used in the middle. Bulbs may be smaller at the ends and larger in the middle.

Various bulb shapes may be used according to several embodiments, including spherical, oblong, egg, and elliptical (e.g., with respect to top view, side-view and/or cross-section). Square, rectangular and diamond-shapes (e.g., with respect to top view, side-view and/or cross-section) are used in some embodiments. Spiral, twisted, or helical bulbs are provided in some embodiments. For example, sphere-like bulbs and oblong bulbs may be used in a single strand. In some embodiments, shapes are alternated. In yet other embodiments, three or more shapes are used in a series, and each series is repeated two, three, four, five, six, seven, or more times. In some embodiments, bulbs of a first shape may be used at the ends, while bulbs of a second shape are used in the middle. Bulbs may be a first shape at the ends and a second shape in the middle, or vice versa.

The positioning of the bulbs may be beneficial for certain vessel sizes and/or clot locations, material, and/or sizes. Bulbs may be touching (e.g., contiguous) or non-touching. A single strand may include bulbs that are both touching and non-touching. In several embodiments, a strand includes bulbs that are all non-touching and/or are spaced apart by one or more spacers. These spacers may be of the same or different material than the bulbs. The spacers may also be shaped differently than the bulbs. The spacers may comprise, be embedded with or coated by markers or other visualization aids (such as radio-opaque portions).

The bulbs may be separated by distances of about 0.1 to 50 mm, including, but not limited to, about 0.5-1, 1-2, 2-3, 3-4, 4-5, 5-8, 8-10, 10-12, 12-15, 15-25, 25-35, and 35-50 mm apart, including overlapping ranges thereof. The spaces between all the bulbs in one strand may be constant. Alternatively, the spacing between two or more (or all) of the bulbs may be different. In some embodiments, some bulbs are spaced the same distance from one another, while other bulbs have different spacing.

Figure 2:
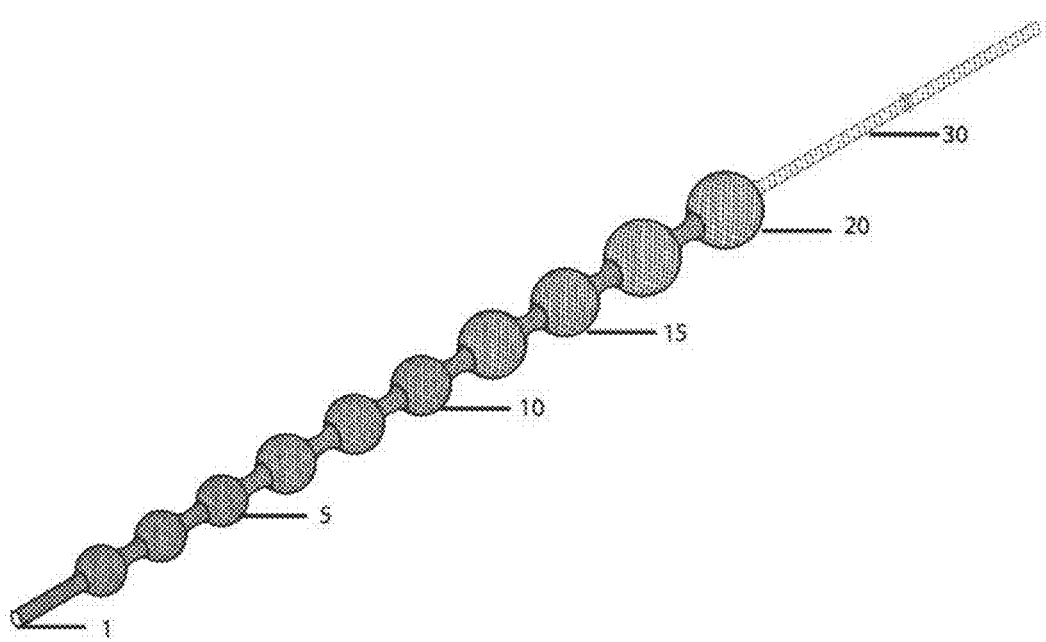
FIG. 2 is a schematic diagram illustrating the 3D perspective view of one of the embodiments with a spherical tapered textile structure.

FIG. 2 is a schematic diagram illustrating the 3D perspective view of one of the embodiments with a spherical tapered textile structure.

Figure 3:
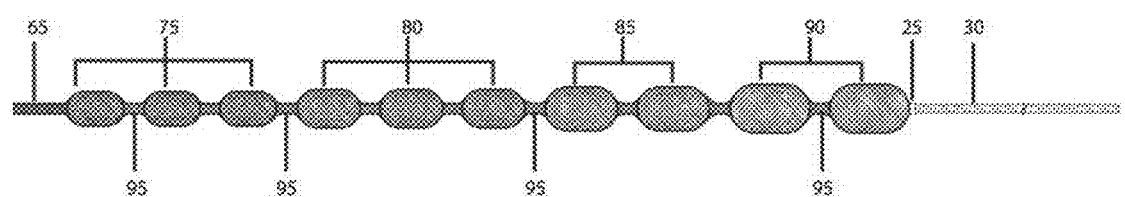
FIG. 3 is a schematic diagram illustrating the 2D view of one of the embodiments with an oblong tapered textile structure.

FIG. 3 is a schematic diagram illustrating the 2D view of one of the embodiments with an oblong tapered textile structure.

Figure 4:
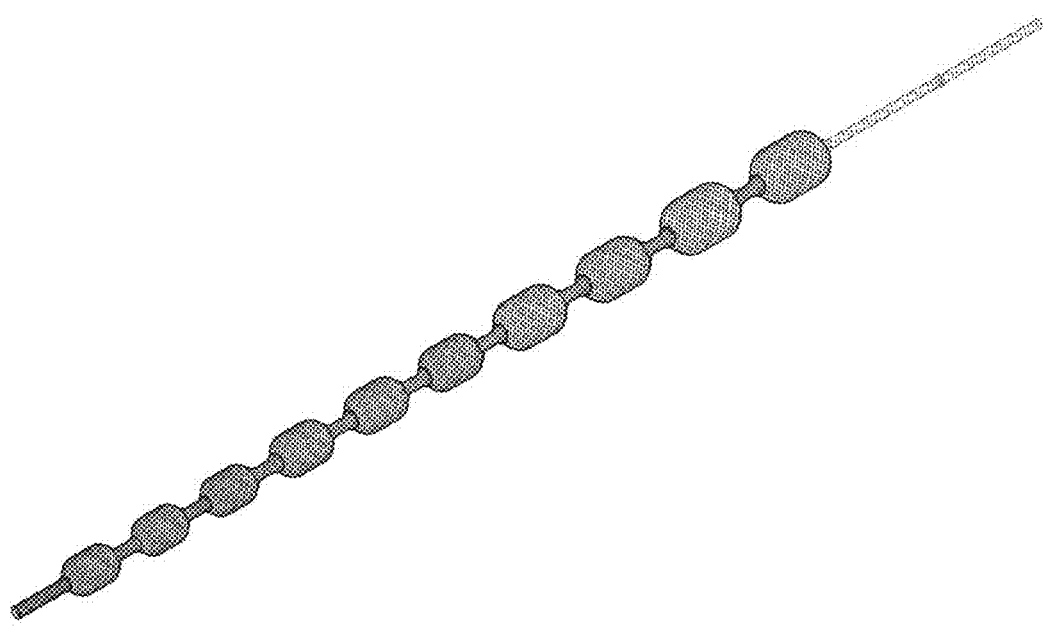
FIG. 4 is a schematic diagram illustrating the 3D perspective view of one of the embodiments with an oblong tapered textile structure.

FIG. 4 is a schematic diagram illustrating the 3D perspective view of one of the embodiments with an oblong tapered textile structure.

Figure 5:
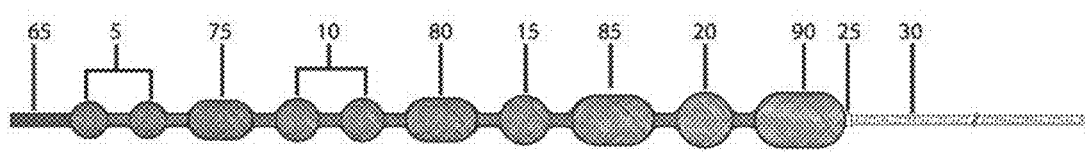
FIG. 5 is a schematic diagram illustrating the 2D view of one of the embodiments with a spherical and oblong interspersed tapered textile structure.

FIG. 5 is a schematic diagram illustrating the 2D view of one of the embodiments with a spherical and oblong interspersed tapered textile structure.

Figure 6:
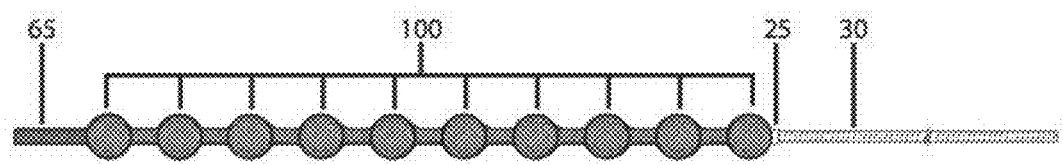
FIG. 6 is a schematic diagram illustrating the 2D view of one of the embodiments with a spherical non-tapered textile structure.

FIG. 6 is a schematic diagram illustrating the 2D view of one of the embodiments with a spherical non-tapered textile structure.

Figure 7:
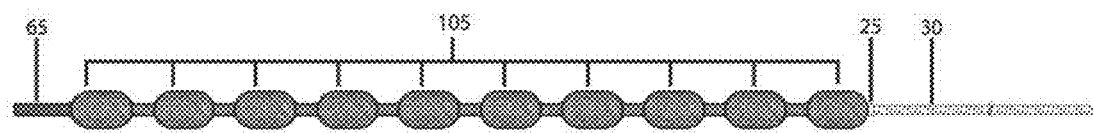
FIG. 7 is a schematic diagram illustrating the 2D view of one of the embodiments with an oblong non-tapered textile structure.

FIG. 7 is a schematic diagram illustrating the 2D view of one of the embodiments with an oblong non-tapered textile structure.

Figure 8:
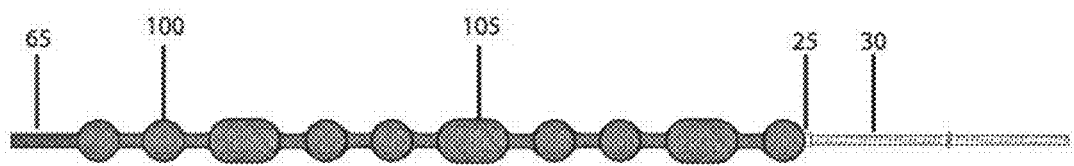
FIG. 8 is a schematic diagram illustrating the 2D view of one of the embodiments with a spherical and oblong interspersed non-tapered textile structure.

FIG. 8 is a schematic diagram illustrating the 2D view of one of the embodiments with a spherical and oblong interspersed non-tapered textile structure.

Figure 9:
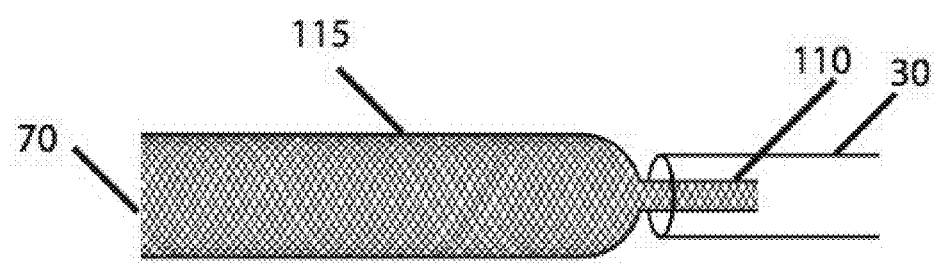
FIG. 9 is a schematic diagram illustrating the 2D view of one of the embodiments with cylindrical wide-mouthed distal tip textile structure.

FIG. 9 is a schematic diagram illustrating the 2D view of one of the embodiments with cylindrical wide-mouthed distal tip textile structure.

Figure 10:
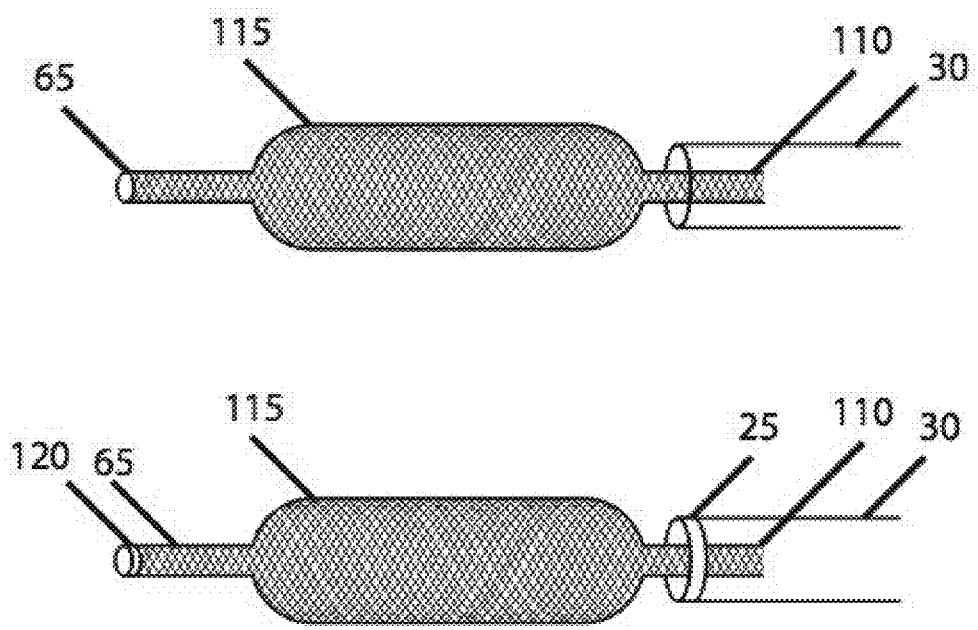
FIG. 10 is a schematic diagram illustrating the 2D view of one of the embodiments with a cylindrical narrow-mouthed distal tip textile structure.

FIG. 10 is a schematic diagram illustrating the 2D view of one of the embodiments with a cylindrical narrow-mouthed distal tip textile structure.

Figure 11:
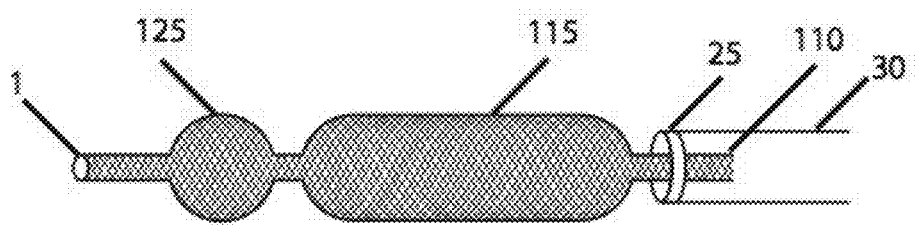
FIG. 11 is a schematic diagram illustrating the 2D view of one of the embodiments with a cylindrical narrow-mouthed distal tip with a spherical or oblong distal filter textile structure.

FIG. 11 is a schematic diagram illustrating the 2D view of one of the embodiments with a cylindrical narrow-mouthed distal tip with a spherical or oblong distal filter textile structure.

Figure 12:
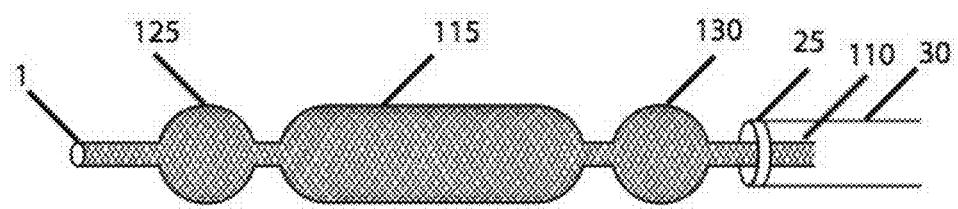
FIG. 12 is a schematic diagram illustrating the 2D view of one of the embodiments with a cylindrical narrow-mouthed distal tip with a spherical distal and proximal filter textile structure.

FIG. 12 is a schematic diagram illustrating the 2D view of one of the embodiments with a cylindrical narrow-mouthed distal tip with a spherical distal and proximal filter textile structure.

Figure 13:
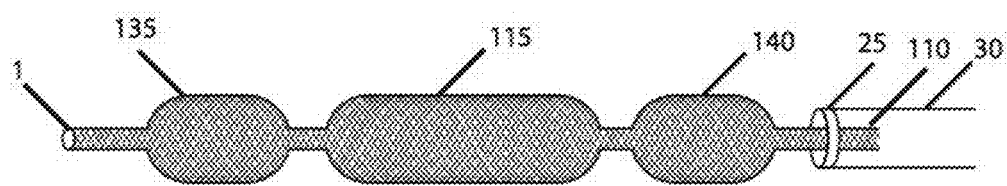
FIG. 13 is a schematic diagram illustrating the 2D view of one of the embodiments with a cylindrical narrow-mouthed distal tip with an oblong distal and proximal filter textile structure.

FIG. 13 is a schematic diagram illustrating the 2D view of one of the embodiments with a cylindrical narrow-mouthed distal tip with an oblong distal and proximal filter textile structure.

Figure 14A:
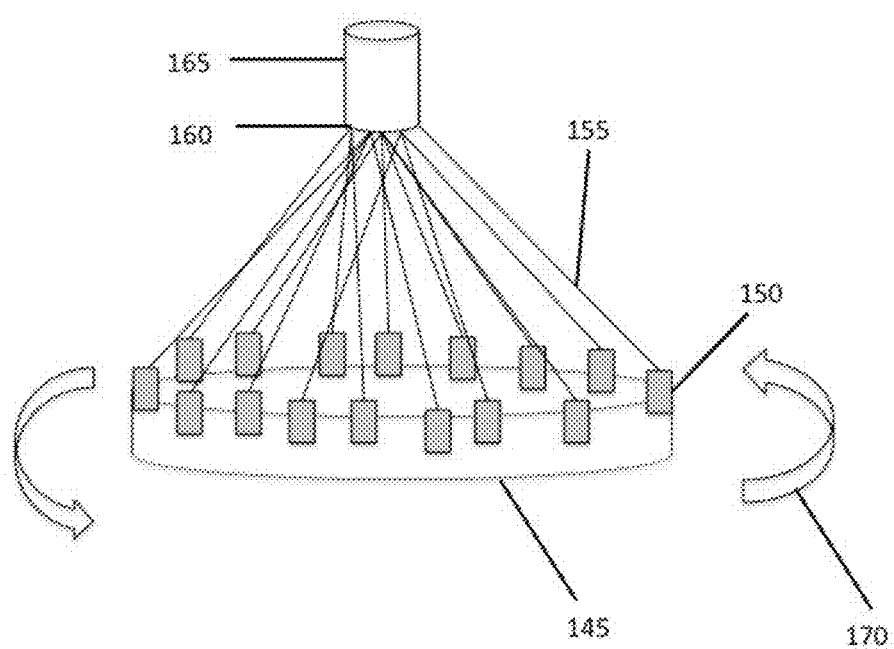
FIG. 14A is a schematic diagram illustrating the wires positioned on the yarn to develop a biomedical textile structure in one of the embodiments.

FIG. 14A is a schematic diagram illustrating the wires positioned on the yarn to develop a biomedical textile structure in one of the embodiments.

Figure 14B:
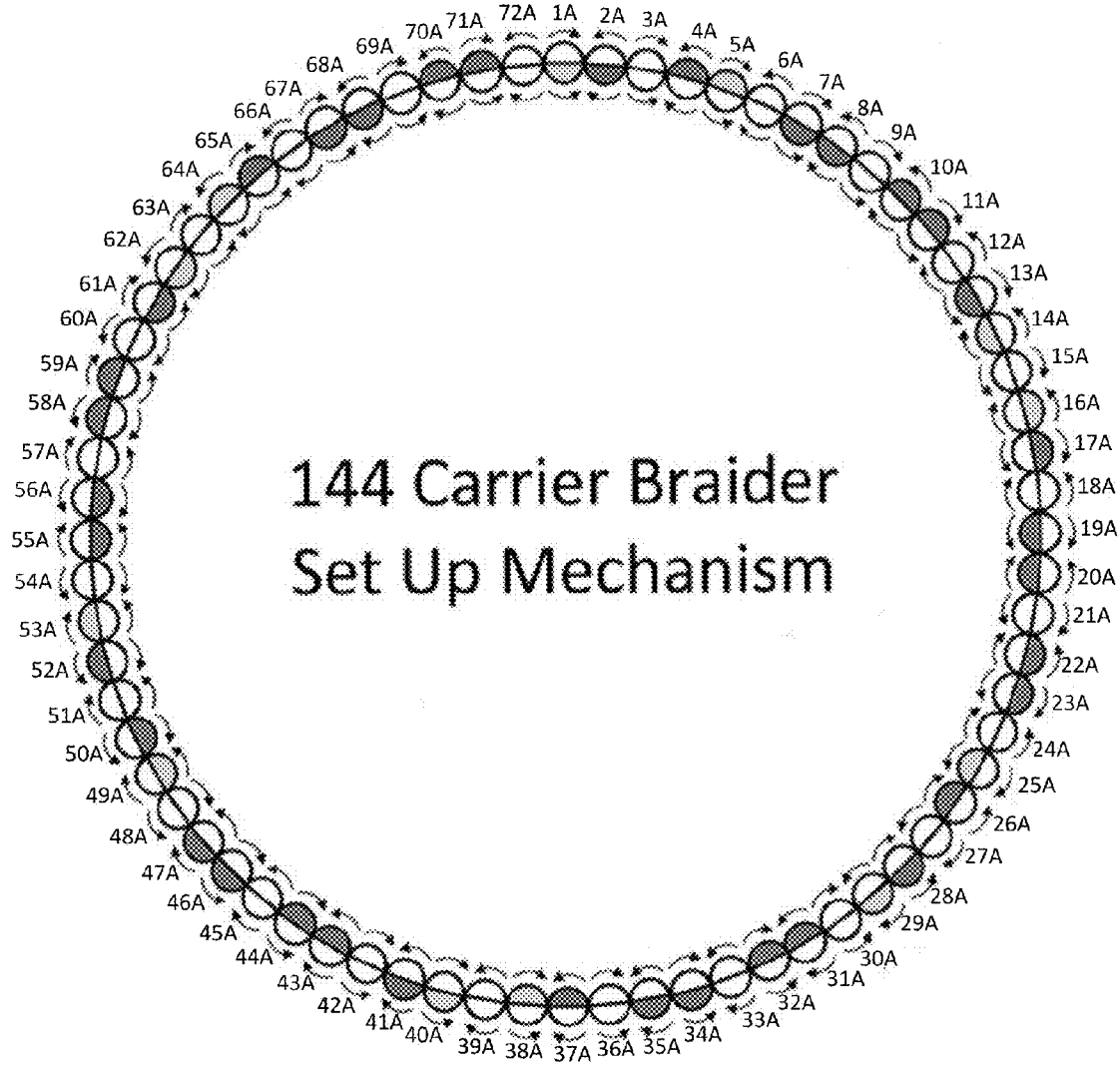
FIG. 14B is a schematic diagram illustrating the braid carrier set up mechanism for the position of the wires on the yarn to develop a biomedical textile structure in one of the embodiments.

FIG. 14B is a schematic diagram illustrating the braid carrier set up mechanism for the position of the wires on the yarn to develop a biomedical textile structure in one of the embodiments.

Figure 15A:
FIG. 15A is a photograph illustrating the wires being braided into a biomedical textile structure on the yarn in one of the embodiments.
Figure 15B:
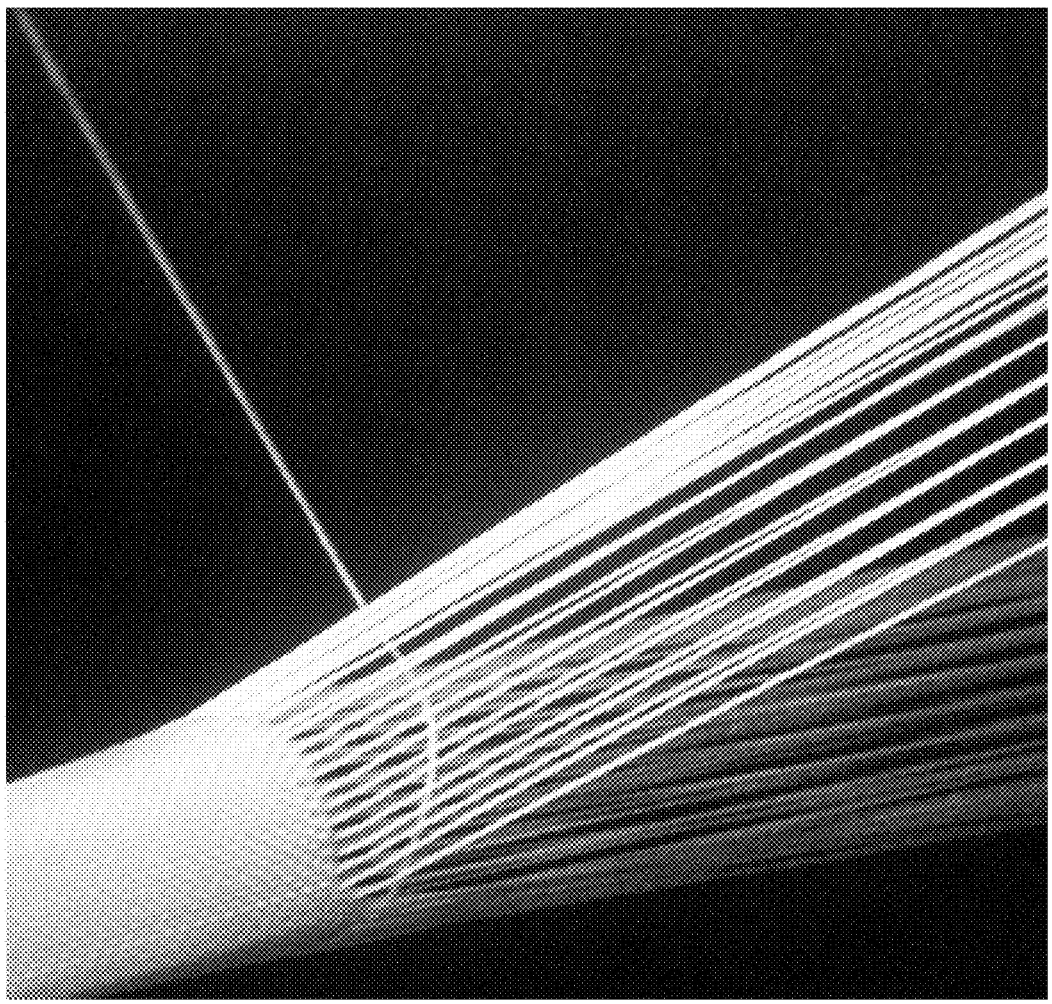
FIG. 15B is a photograph illustrating the wires being knitted into a biomedical textile structure in one of the embodiments.
Figure 15C:
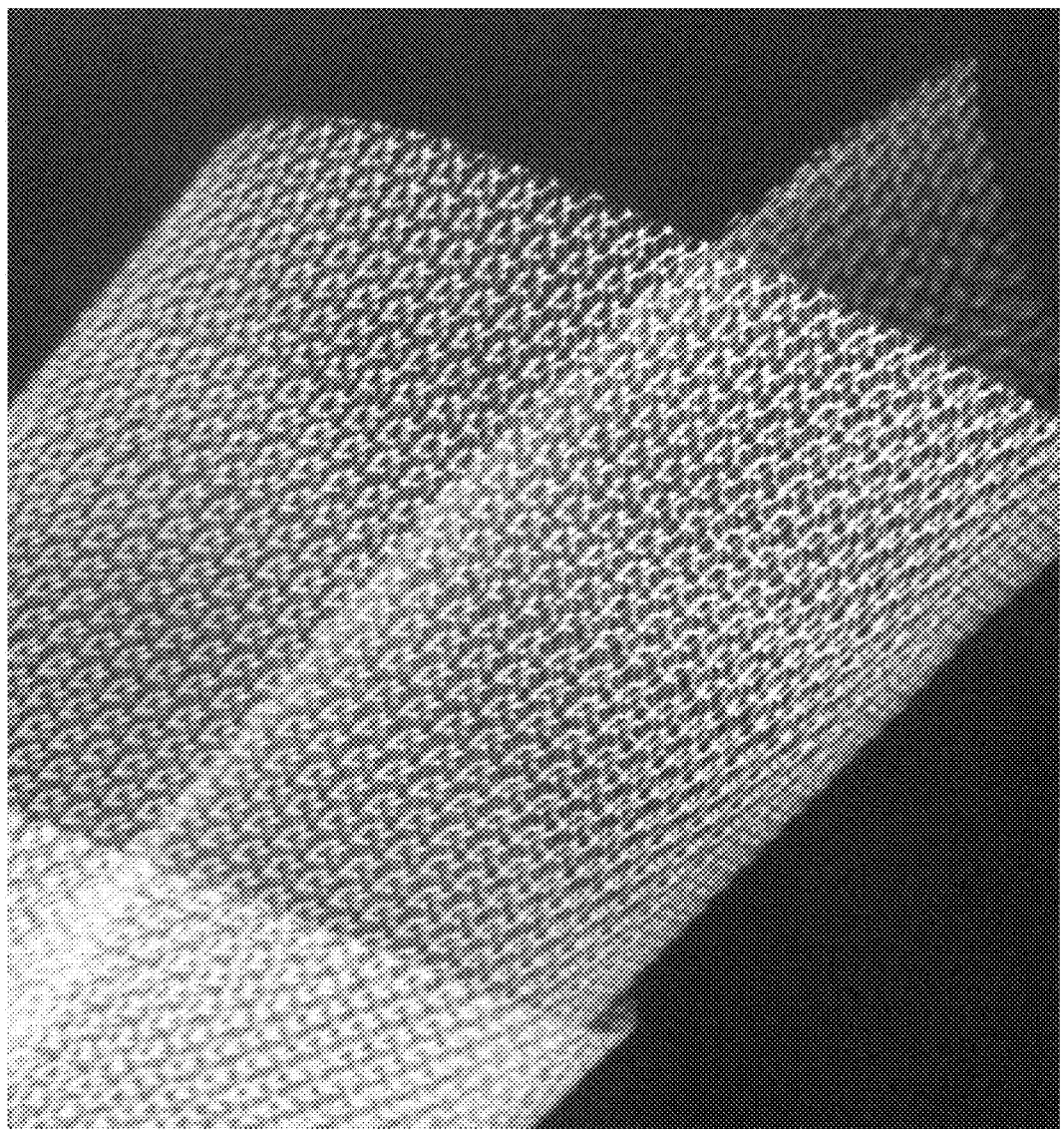
FIG. 15C is a photograph illustrating the wires being woven into a biomedical textile structure in one of the embodiments.

FIG. 15A is a photograph illustrating the wires being braided into a biomedical textile structure on the yarn in one of the embodiments. FIG. 15B is a photograph illustrating the wires being knitted into a biomedical textile structure in one of the embodiments. FIG. 15C is a photograph illustrating the wires being woven into a biomedical textile structure in one of the embodiments.

Figure 16:
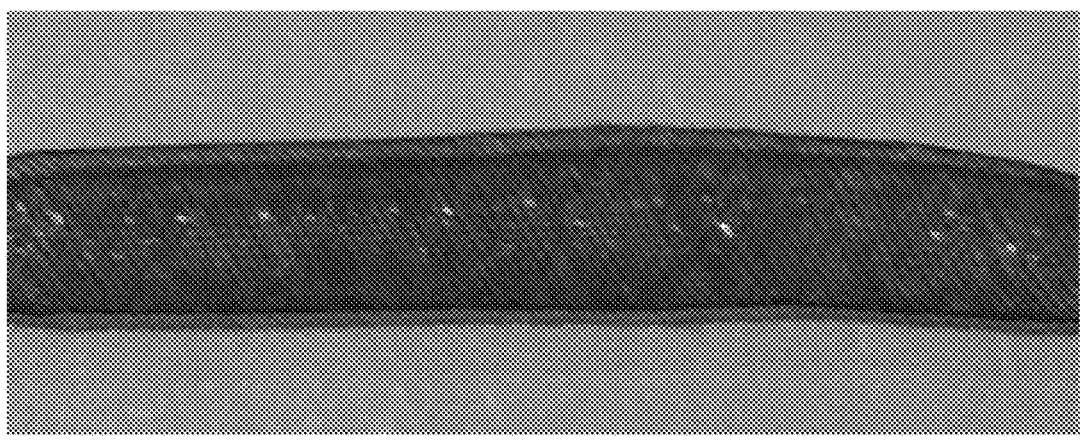
FIG. 16 is a photograph illustrating the primary tubular shape set textile structure in one of the embodiments.

FIG. 16 is a photograph illustrating the primary tubular shape set textile structure in one of the embodiments.

Figure 17:
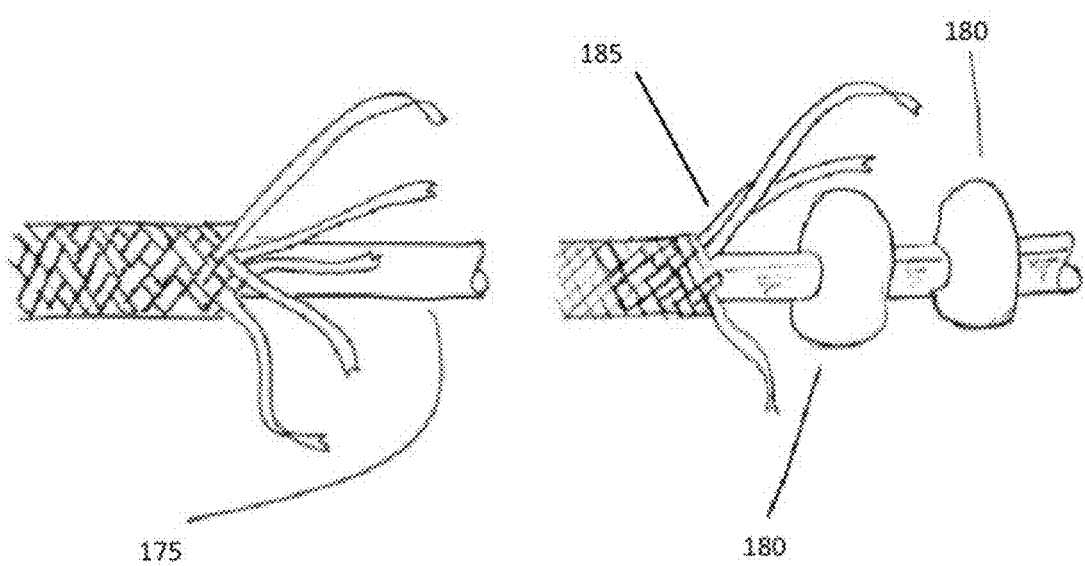
FIG. 17 is a schematic diagram illustrating the primary shape setting into the necessary geometries needed to develop the shape-set textile structures in one of the embodiments.

FIG. 17 is a schematic diagram illustrating the primary shape setting into the necessary geometries needed to develop the shape-set textile structures in one of the embodiments.

Figure 18:
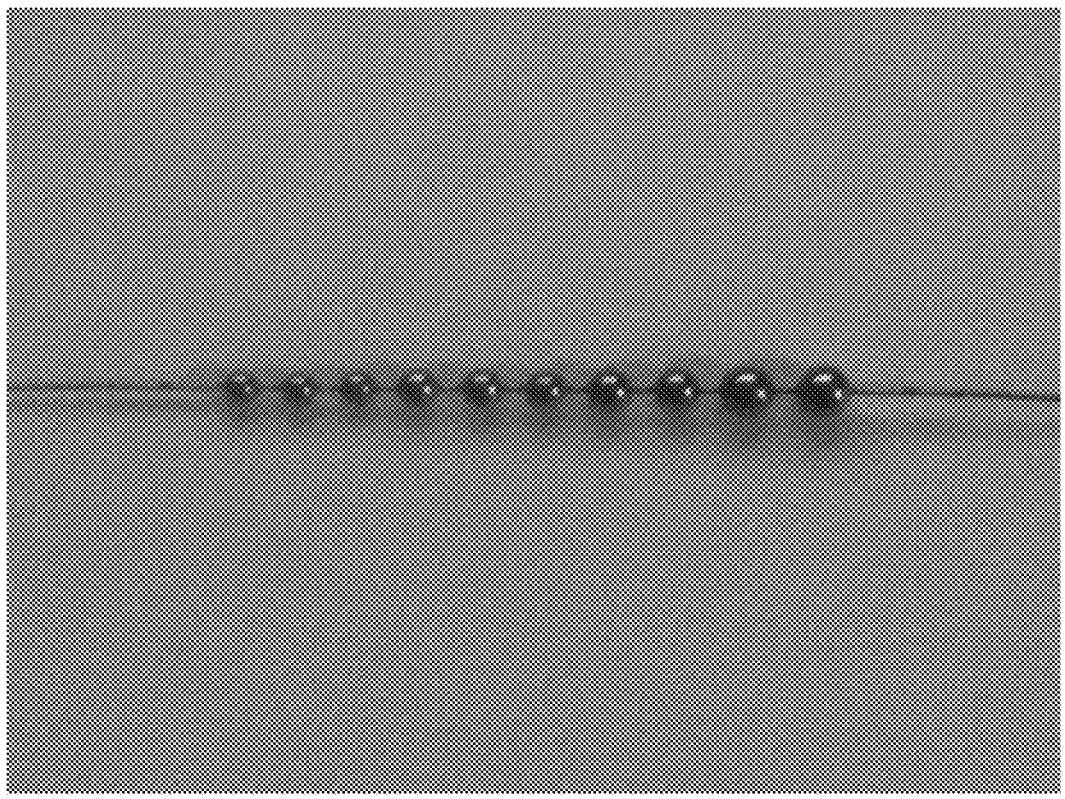
FIG. 18 is a photograph illustrating the mandrel used for braiding on the yarn that is then used for primary shape setting into the necessary geometries needed in one of the embodiments.

FIG. 18 is a photograph illustrating the mandrel used for braiding on the yarn that is then used for primary shape setting into the necessary geometries needed in one of the embodiments.

Figure 19:
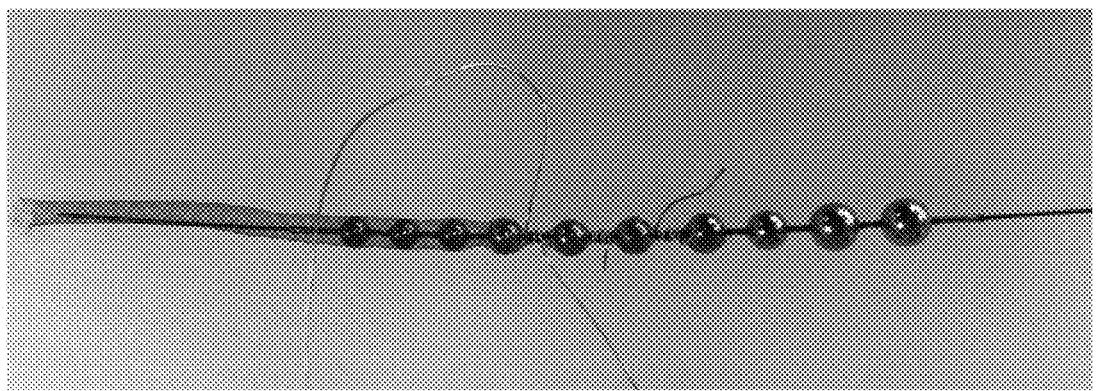
FIG. 19 is a photograph illustrating secondary shape setting into the necessary geometries needed to develop the shape-set textile structure in one of the embodiments.

FIG. 19 is a photograph illustrating secondary shape setting into the necessary geometries needed to develop the shape-set textile structure in one of the embodiments.

Figure 20:
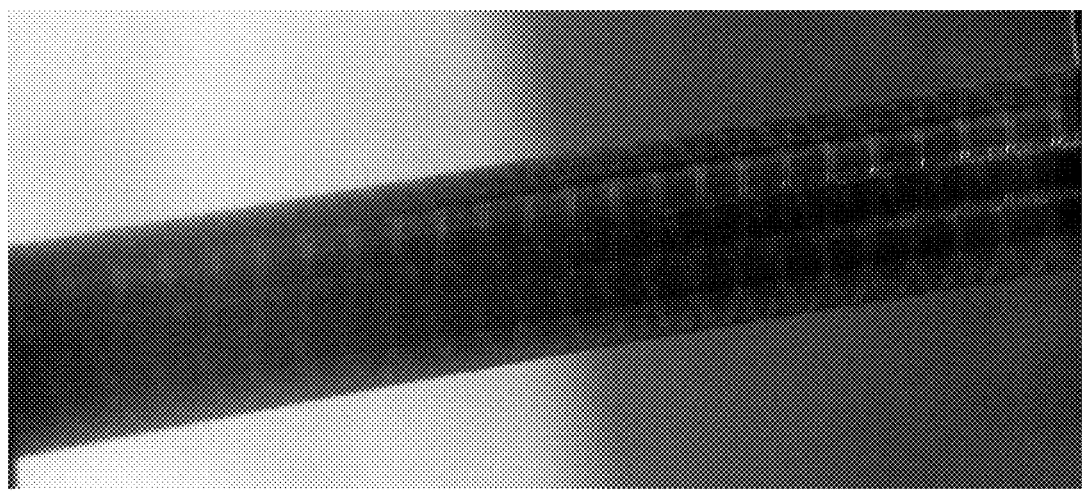
FIG. 20 is an X-ray photograph illustrating one of the embodiments where there is grouping of multiple radioopaque filaments or wires together to form an inter-twining thick band for maximal radio-opacity during fluoroscopy.

FIG. 20 is an X-ray photograph illustrating one of the embodiments where there is grouping of multiple radio-opaque filaments or wires together to form an inter-twining thick band for maximal radio-opacity during fluoroscopy.

Radio-opaque materials, metals or alloys, including but not limited to iridium, platinum, tantalum, gold, palladium, tungsten, tin, silver, titanium, nickel, zirconium, rhenium, bismuth, molybdenum, or combinations of the above etc. to enable visibility during interventional procedures.

Figure 21:
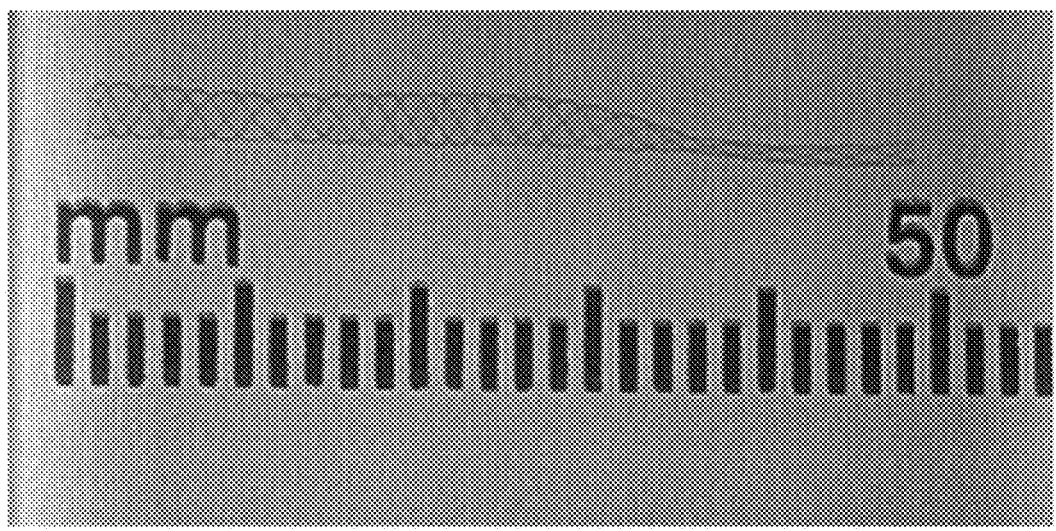
FIG. 21 is an X-ray photograph illustrating single filaments inter-twined to provide radio-opacity during fluoroscopy in one of the embodiments.

FIG. 21 is an X-ray photograph illustrating single filaments inter-twined to provide radio-opacity during fluoroscopy in one of the embodiments.

Figure 22:
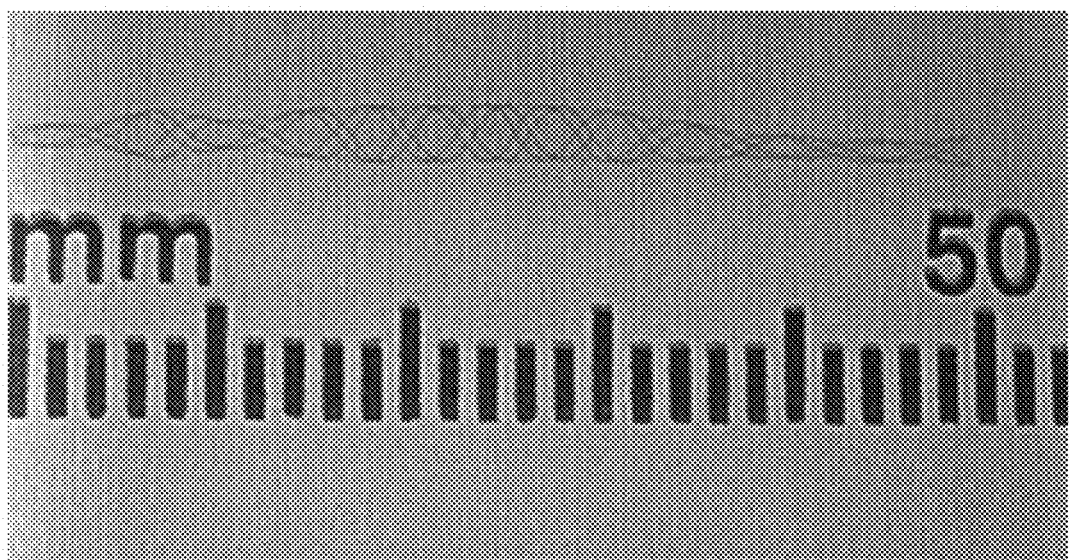
FIG. 22 is an X-ray photograph illustrating double filaments inter-twined to provide radio-opacity during fluoroscopy in one of the embodiments.

FIG. 22 is an X-ray photograph illustrating double filaments inter-twined to provide radio-opacity during fluoroscopy in one of the embodiments.

Figure 23:
FIG. 23 is a photograph illustrating the need for post-processing of the free end of the textile structure to keep the filaments or wires from fraying in one of the embodiments.

FIG. 23 is a photograph illustrating the need for post-processing of the free end of the textile structure to keep the filaments or wires from fraying in one of the embodiments. Post-processing of the free end of the textile structure (e.g., the elongate support structure and the bulbs) in some of the embodiments includes dip coating, spray coating, sandwich welding the free end using radio-opaque marker bands. Radio-opaque marker band materials, metals or alloys, including but not limited to iridium, platinum, tantalum, gold, palladium, tungsten, tin, silver, titanium, nickel, zirconium, rhenium, bismuth, molybdenum, or combinations of the above etc. to enable visibility during interventional procedures. In some of the embodiments, radio-opaque marker bands can be sandwich welded to the free end of the textile structure (e.g., the elongate support structure and the bulbs), butt welded to the distal end of the delivery system/hypotube, bonded or soldered to the delivery system or hypotube at regular intervals or laser welded into the kerfs created in the laser cut pattern at regular intervals to help measure a clot length, such radio-opaque markers at regular intervals may be separated by distances of about 0.1 to 50 mm, including, but not limited to, about 0.5-1, 1-2, 2-3, 3-4, 4-5, 5-8, 8-10, 10-12, 12-15, 15-25, 25-35, and 35-50 mm apart, including overlapping ranges thereof.

The dip coating or spray coating may comprise a biomedical polymer, e.g., silicone, polyurethane, polyethylene (Rexell™ made by Huntsman), polypropylene, polyester (Hytril™ made by Dupont), poly tetra fluoro-ethylene (PTFE), polyvinyl chloride (PVC), polyamides (Durethan™ made by Bayer), polycarbonate (Corethane™ made by Corvita Corp), or polyethylene-terephthalate. The dip coating or spray coating may further comprise a radio-opaque material, e.g., particles of tantalum, particles of gold, other radio-opaque agents, e.g., barium sulfate, tungsten powder, bismuth subcarbonate, bismuth oxychloride, iodine containing agents such as iohexol (Omnipaque™ Amersham Health).

Figure 24:
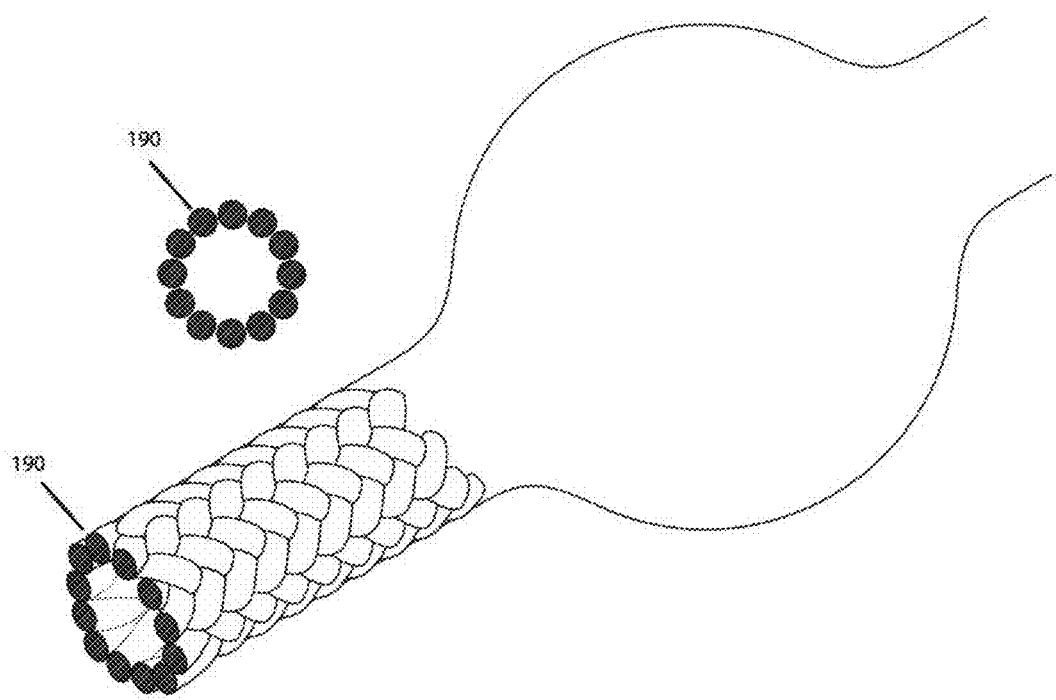
FIG. 24 is a schematic diagram illustrating the appearance of the free end of the textile structure after laser cutting the free end to keep the filaments or wires from fraying in one of the embodiments.

FIG. 24 is a schematic diagram illustrating the appearance of the free end of the textile structure (e.g., the elongate support structure and the bulbs) after laser cutting the free end to keep the filaments or wires from fraying in one of the embodiments.

Figure 25:
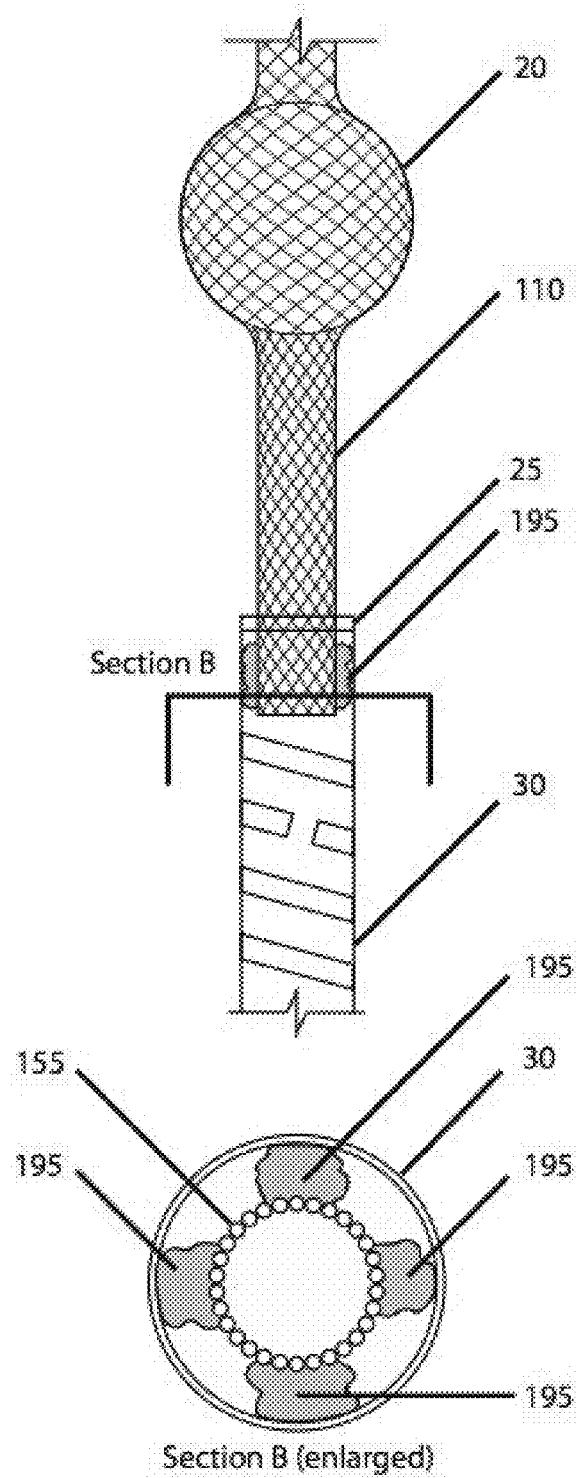
FIG. 25 is a schematic diagram illustrating the inlay bonding approach between the shape-set textile structure and the delivery system using solder in one of the embodiments.

FIG. 25 is a schematic diagram illustrating the inlay bonding approach between the shape-set textile structure (e.g., the elongate support structure and the bulbs) and the delivery system (e.g., a hypotube, wire or multi-filament hybrid) using solder in one of the embodiments. The solder may be a silver-based lead free solder in some embodiments. The shape-set textile structure may be substantially or fully oxide free when bonding the shape-set textile structure to the delivery system when using such solder.

Figure 26:
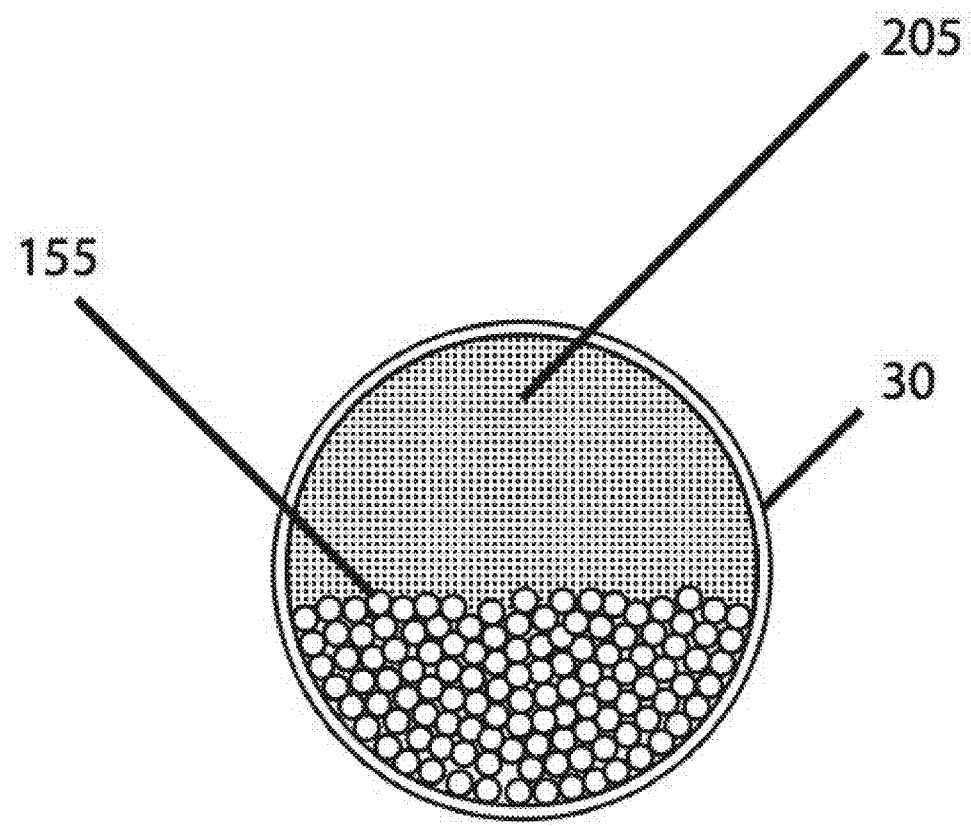
FIG. 26 is a schematic diagram illustrating the overall ratio of the cross-sectional area between the filaments or wires of the textile structure and the bonding agent in one of the embodiments.

FIG. 26 is a schematic diagram illustrating the overall ratio of the cross-sectional area between the filaments or wires of the textile structure (e.g., the elongate support structure and the bulbs) and the bonding agent in one of the embodiments.

Figure 27A:
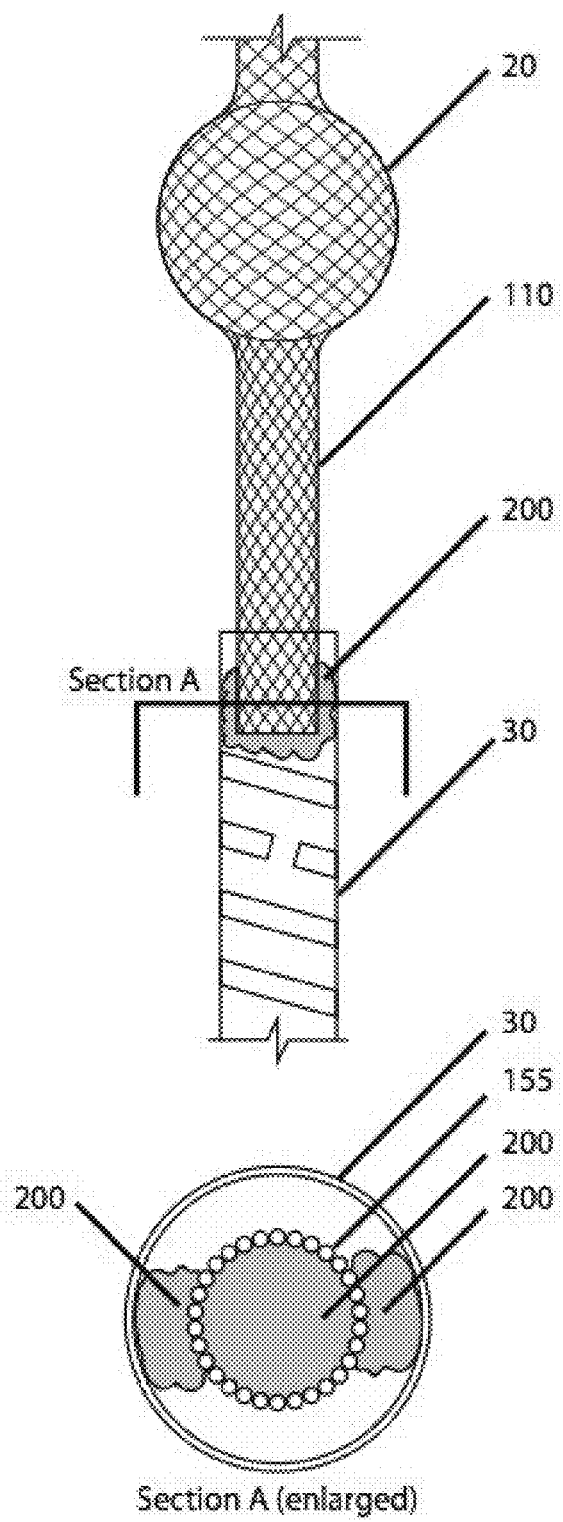
FIG. 27A is a schematic diagram illustrating the inlay bonding approach between the shape-set textile structure and delivery system using epoxy agents in one of the embodiments.
Figure 27B:
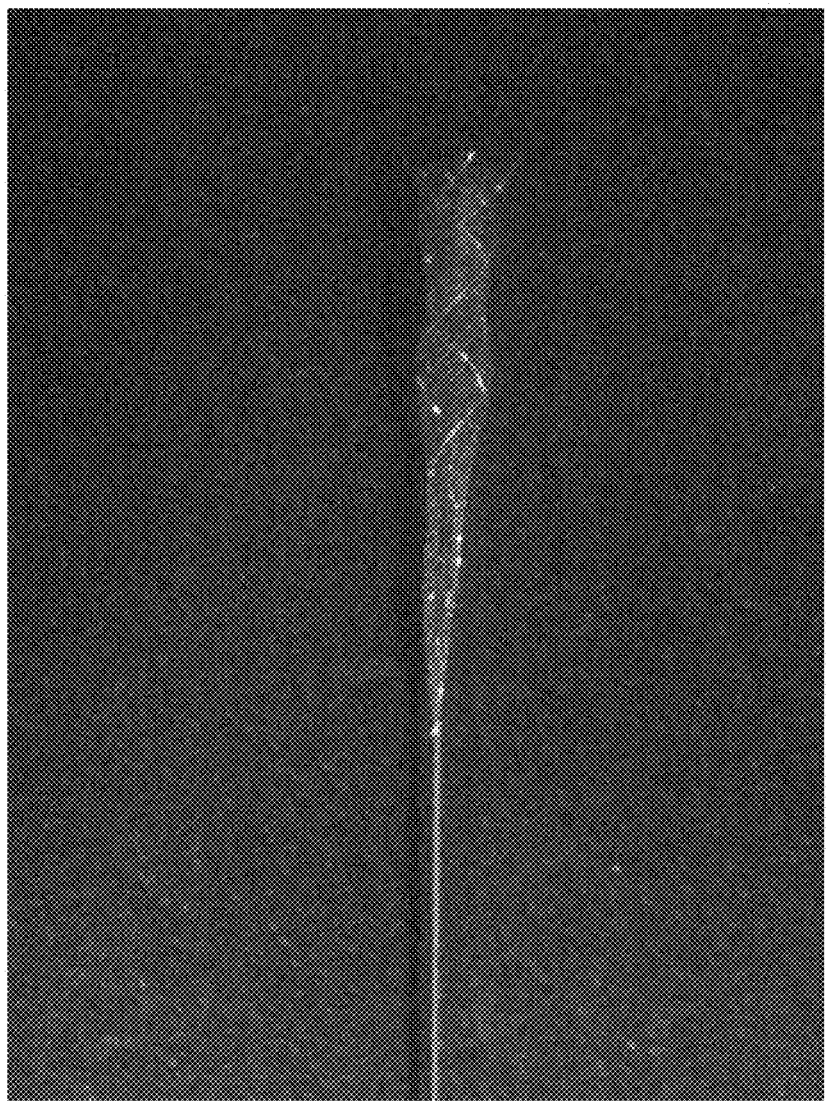
FIG. 27B is a photograph illustrating the inlay bonding approach between the shape-set textile structure and delivery system using epoxy agents in one of the embodiments.

FIG. 27A is a schematic diagram illustrating the inlay bonding approach between the shape-set textile structure and delivery system using epoxy agents in one of the embodiments. FIG. 27B is a photograph illustrating the inlay bonding approach between the shape-set textile structure and delivery system using epoxy agents in one of the embodiments.

Figure 28:
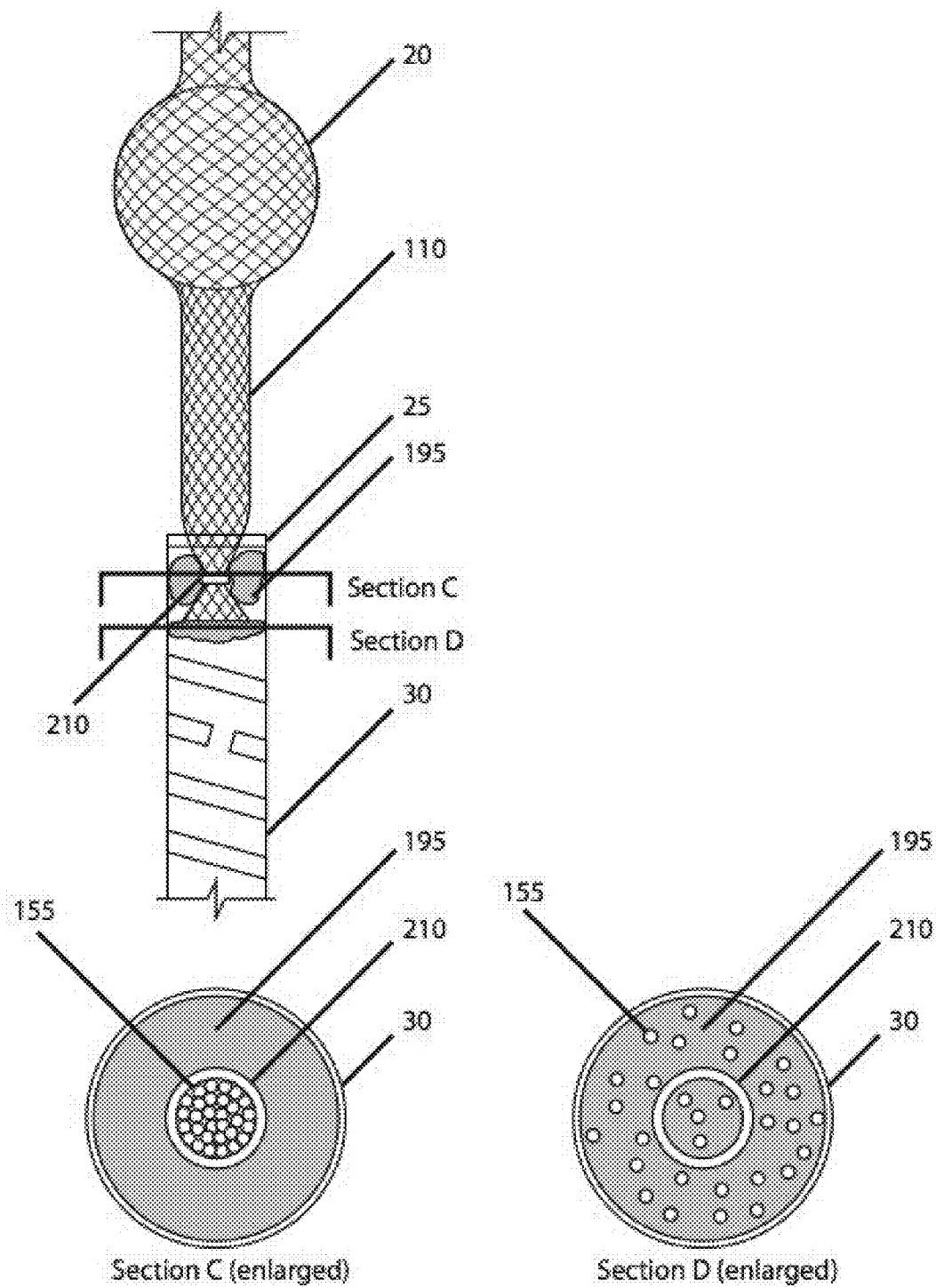
FIG. 28 is a schematic diagram illustrating the inlay bonding approach between the shape-set textile structure and delivery system using a pinched ring as well as a bonding agent in one of the embodiments.

FIG. 28 is a schematic diagram illustrating the inlay bonding approach between the shape-set textile structure (e.g., the elongate support structure and the bulbs) and delivery system using a pinched ring as well as a bonding agent in one of the embodiments.

Figure 29:
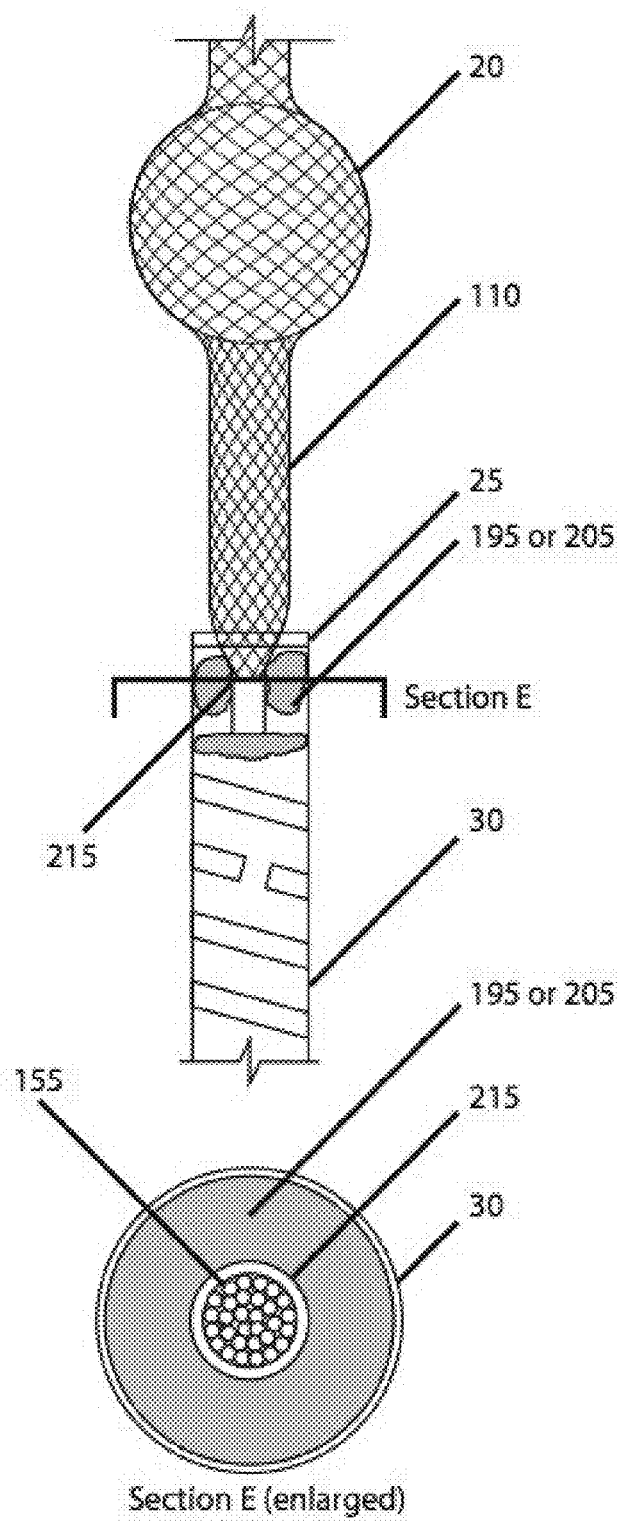
FIG. 29 is a schematic diagram illustrating the inlay bonding approach between the shape-set textile structure and delivery system using a pinched tube as well as a bonding agent in one of the embodiments.

FIG. 29 is a schematic diagram illustrating the inlay bonding approach between the shape-set textile structure (e.g., the elongate support structure and the bulbs) and delivery system (e.g., a hypotube, wire or multi-filament hybrid) using a pinched tube as well as a bonding agent in one of the embodiments. In some of the embodiments, inlay bonding approach includes laser welding, laser butt welding, laser rivet welding, and mechanical crimping of a flared distal end of the hypotube on the inlayed proximal neck of the textile structure (e.g., the elongate support structure and the bulbs).

Figure 30:
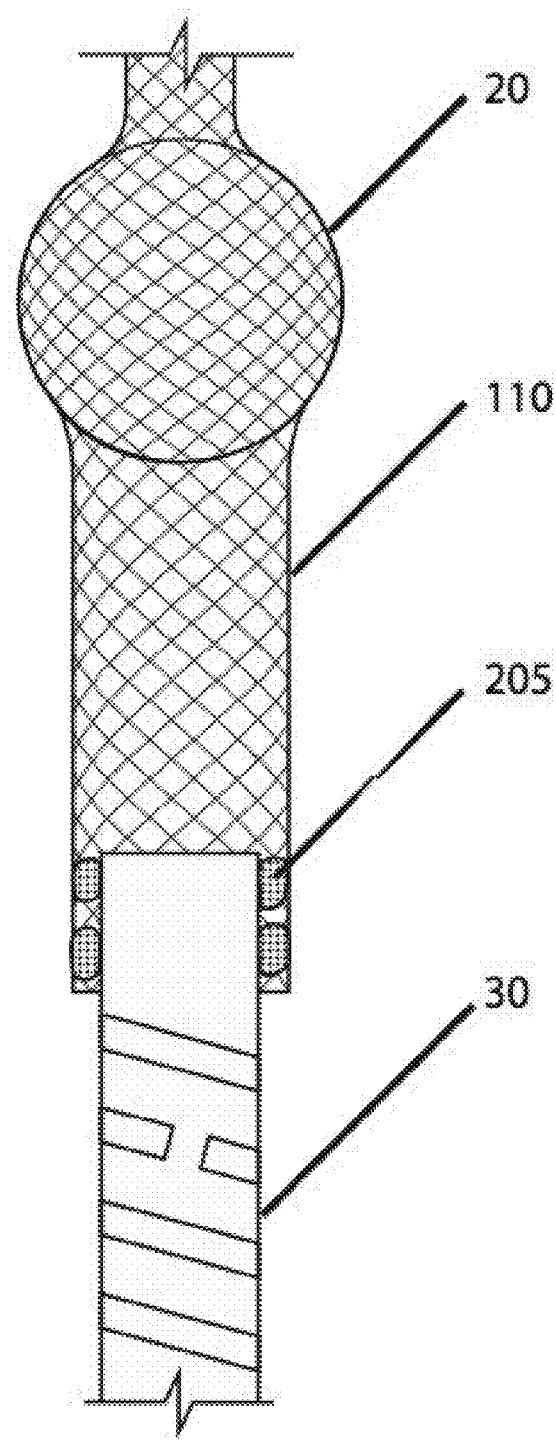
FIG. 30 is a schematic diagram illustrating the overlay bonding approach between the proximal neck of the shape-set textile structure and the distal end of the delivery system using solder in one of the embodiments.

FIG. 30 is a schematic diagram illustrating the overlay bonding approach between the proximal neck of the shape-set textile structure (e.g., the elongate support structure and the bulbs) and the distal end of the delivery system (e.g., a hypotube, wire or multi-filament hybrid) using solder in one of the embodiments.

Figure 31:
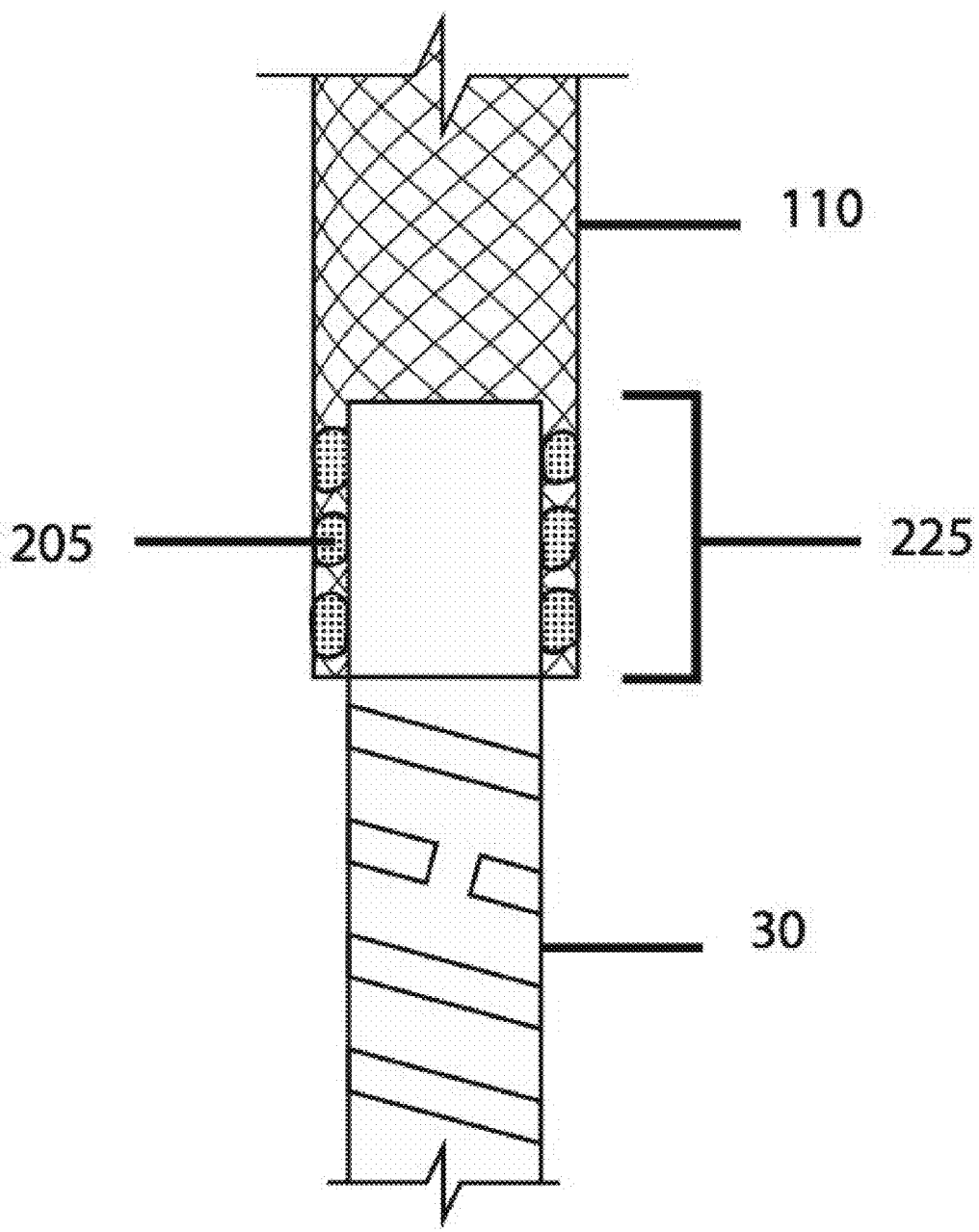
FIG. 31 is a schematic diagram illustrating the overlay bonding approach between the proximal neck of the shape-set textile structure and the distal end of the delivery system using epoxy in one of the embodiments.

FIG. 31 is a schematic diagram illustrating the overlay bonding approach between the proximal neck of the shape-set textile structure (e.g., the elongate support structure and the bulbs) and the distal end of the delivery system (e.g., a hypotube, wire or multi-filament hybrid) using epoxy in one of the embodiments.

Figure 32:
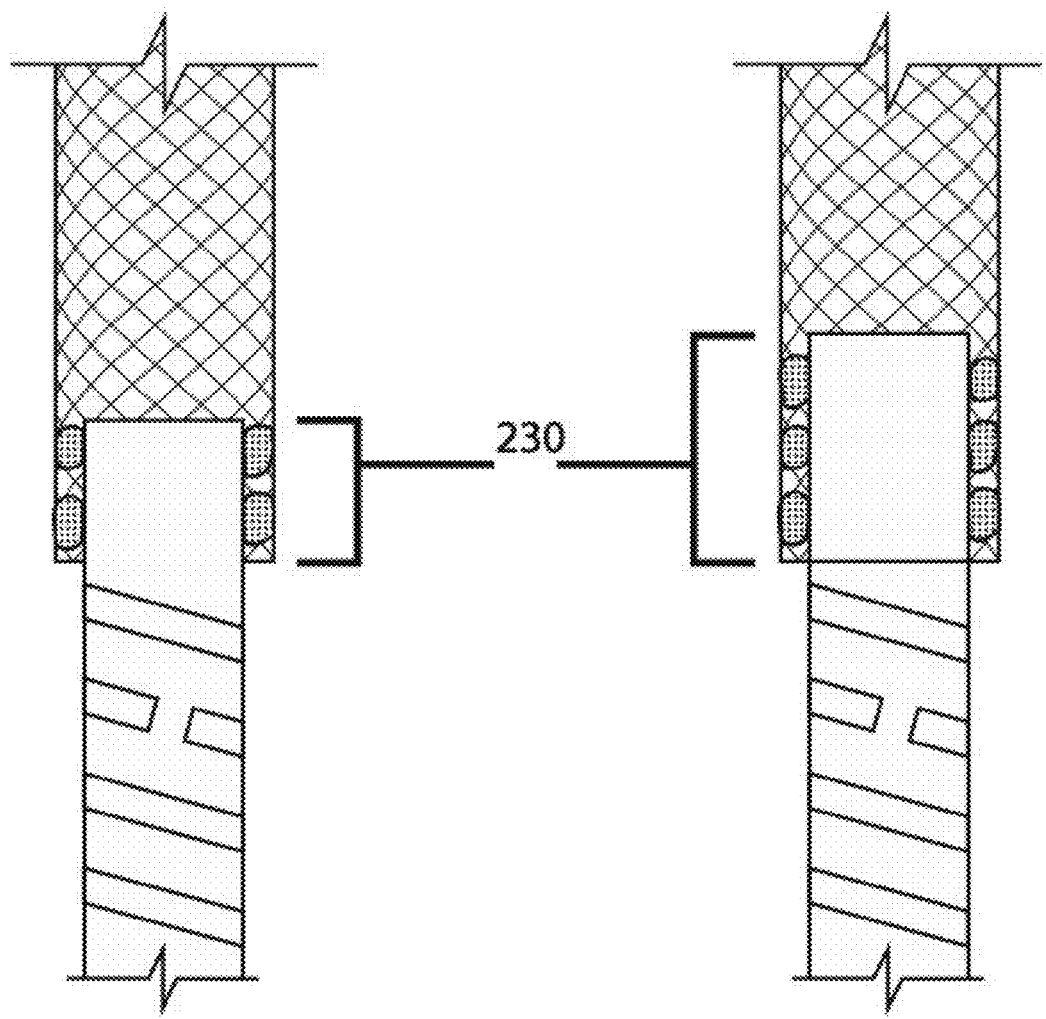
FIG. 32 is a schematic diagram illustrating the overlay bonding approach between the proximal neck of the shape-set textile structure and the non-laser cut distal tip of the delivery system using epoxy in one of the embodiments.

FIG. 32 is a schematic diagram illustrating the overlay bonding approach between the proximal neck of the shape-set textile structure (e.g., the elongate support structure and the bulbs) and the non-laser cut distal tip of the delivery system (e.g., a hypotube, wire or multi-filament hybrid) using epoxy in one of the embodiments.

Figure 33:
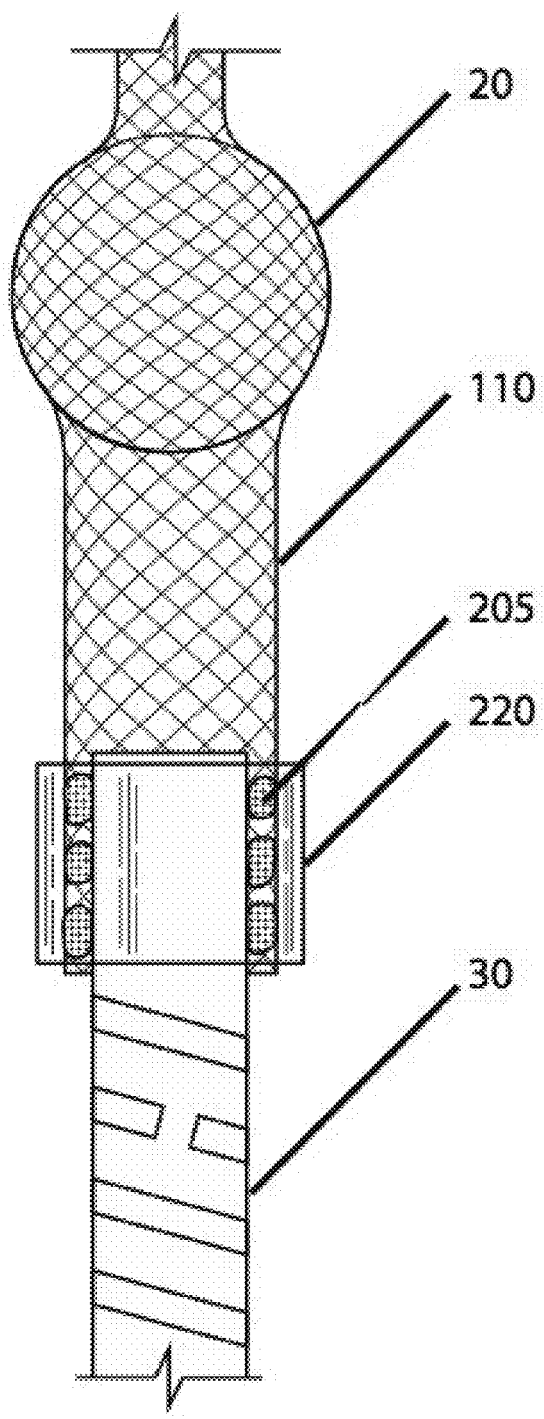
FIG. 33 is a schematic diagram illustrating the overlay bonding approach between the proximal neck of the shape-set textile structure and the distal end of the delivery system using epoxy and heat shrink tubing in one of the embodiments.

FIG. 33 is a schematic diagram illustrating the overlay bonding approach between the proximal neck of the shape-set textile structure (e.g., the elongate support structure and the bulbs) and the distal end of the delivery system (e.g., a hypotube, wire or multi-filament hybrid) using epoxy and heat shrink tubing in one of the embodiments.

Figure 34:
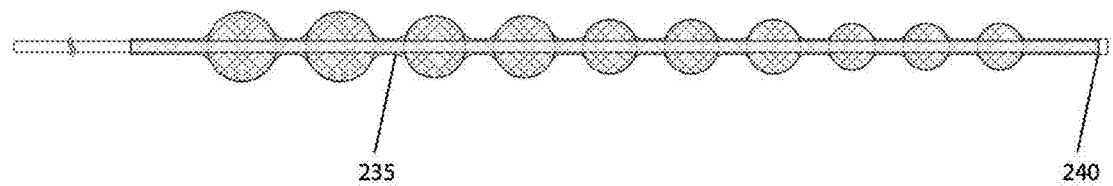
FIG. 34 is a schematic diagram illustrating the overlay bonding approach between the distal neck of the shape-set textile structure and the distal end of the delivery system using bonding agent in one of the embodiments.

FIG. 34 is a schematic diagram illustrating the overlay bonding approach between the distal neck of the shape-set textile structure (e.g., the elongate support structure and the bulbs) and the distal end of the delivery system (e.g., a hypotube, wire or multi-filament hybrid) using bonding agent in one of the embodiments. In some of the embodiments, overlay bonding approach includes laser welding, laser butt welding, laser rivet welding, and mechanical crimping of a flared distal end of the hypotube on the inlayed proximal neck of the textile structure (e.g., the elongate support structure and the bulbs).

Figure 35:
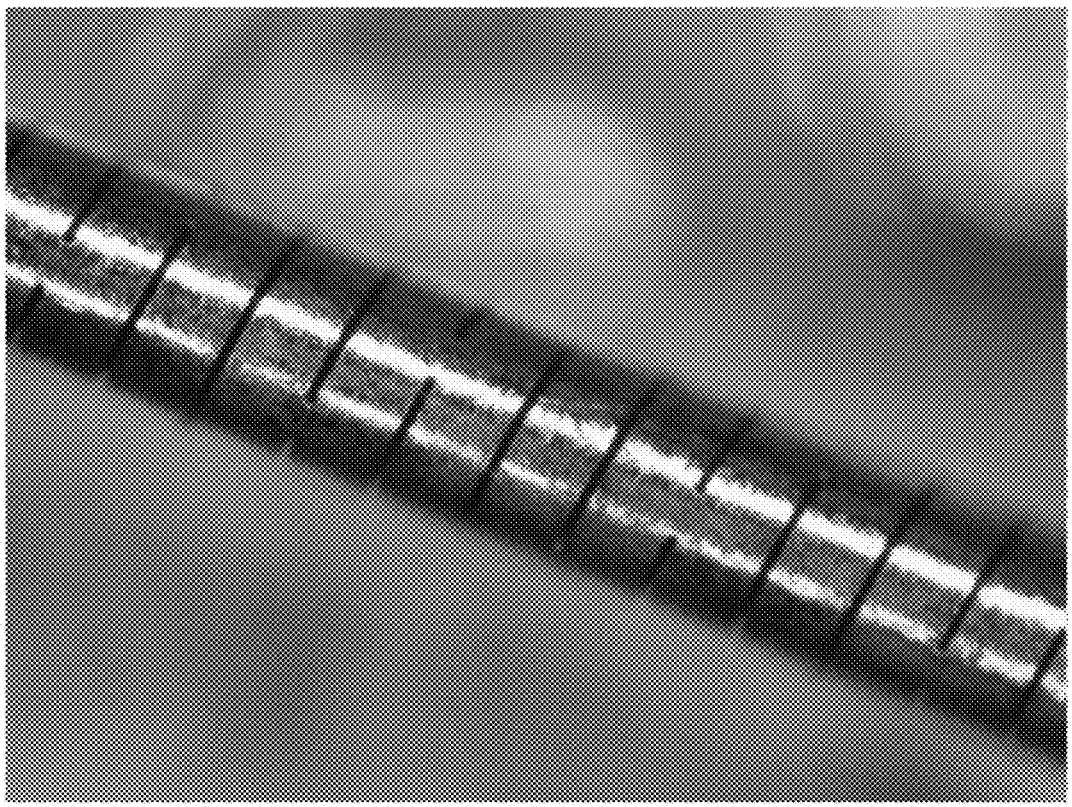
FIG. 35 is a photography illustrating the angled flexible laser-cut hypotube delivery system in one of the embodiments.

FIG. 35 is a photography illustrating the angled flexible laser-cut hypotube delivery system in one of the embodiments.

Various components (e.g., the elongate support structure, the bulbs, the sheath or the delivery system such as the hypotube) may be made up of materials that are biocompatible or surface treated to produce biocompatibility. Suitable materials include e.g., platinum, titanium, nickel, chromium, cobalt, tantalum, tungsten, iron, manganese, molybdenum, and alloys thereof including nitinol, chromium cobalt, stainless steel, etc. Suitable materials also include combinations of metals and alloys. Suitable materials also include polymers such as polylactic acid (PLA), polyglycolic acid (PGA), polyclycoloc-lactic acid (PLGA), polycaprolactone (PCL), polyorthoesters, polyanhydrides, and copolymers thereof. In some embodiments, the thrombectomy device is made of nitinol and platinum tungsten.

Figure 36:
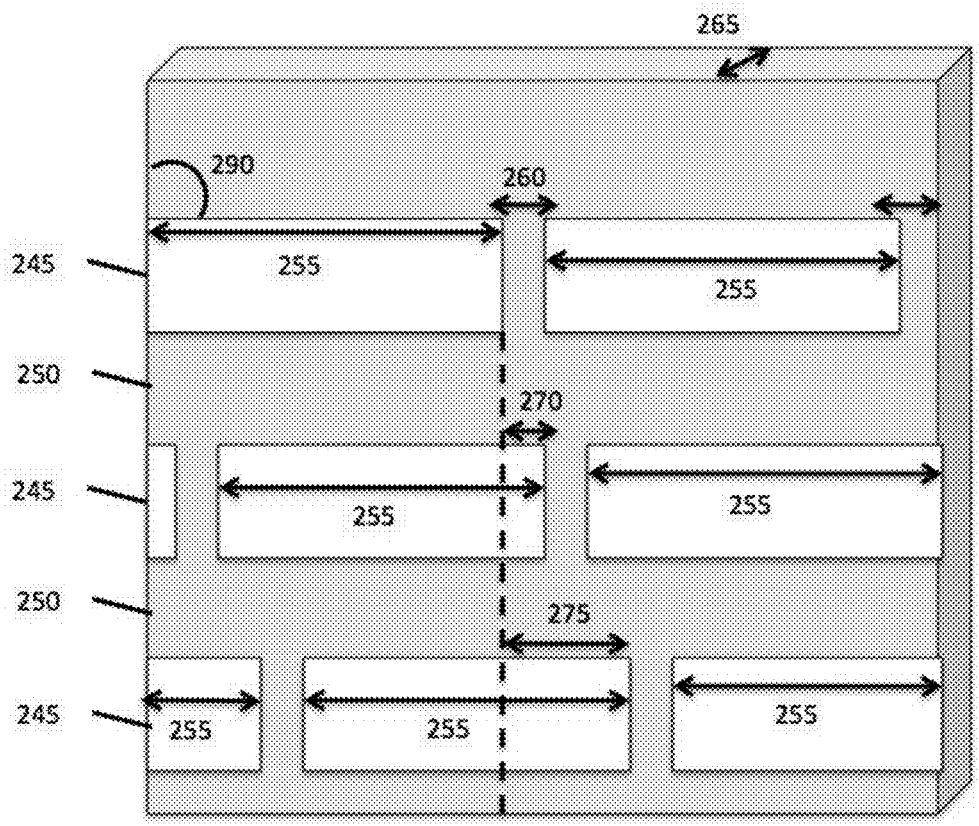
FIG. 36 is a schematic diagram illustrating dimensions for laser-cut Pattern A in one of the embodiments.

FIG. 36 is a schematic diagram illustrating dimensions for laser-cut Pattern A in one of the embodiments.

Figure 37:
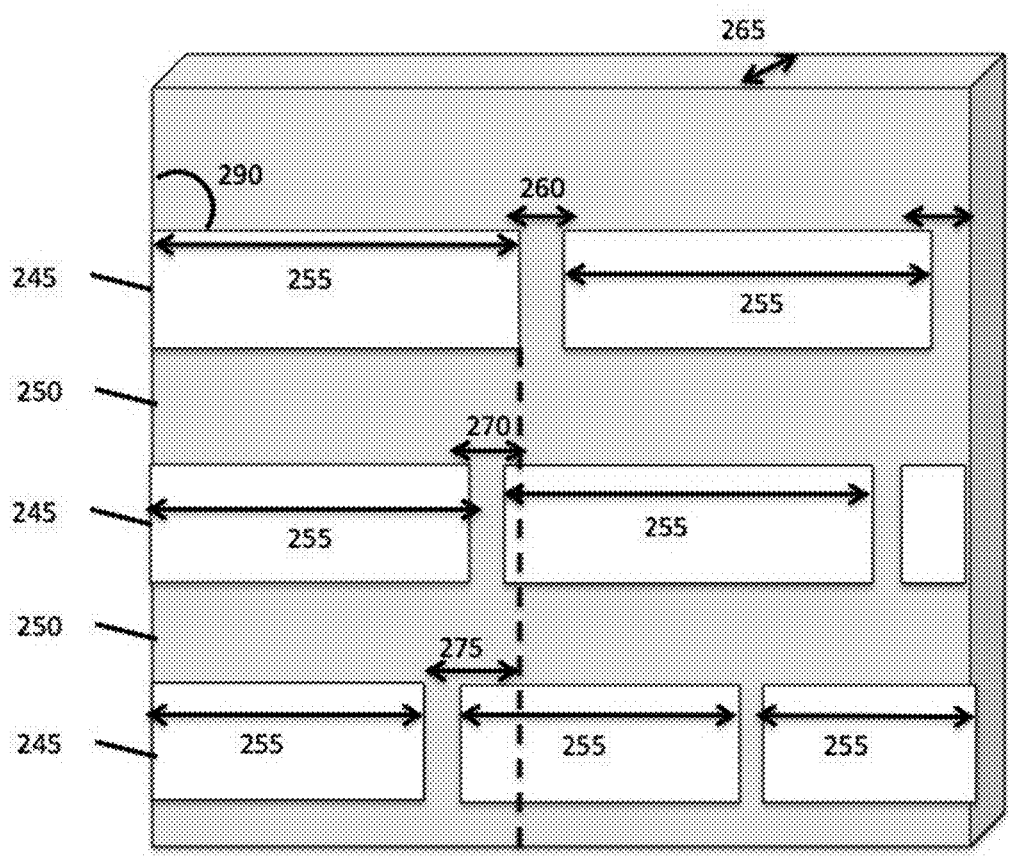
FIG. 37 is a schematic diagram illustrating dimensions for laser-cut Pattern B in one of the embodiments.

FIG. 37 is a schematic diagram illustrating dimensions for laser-cut Pattern B in one of the embodiments.

Figure 38:
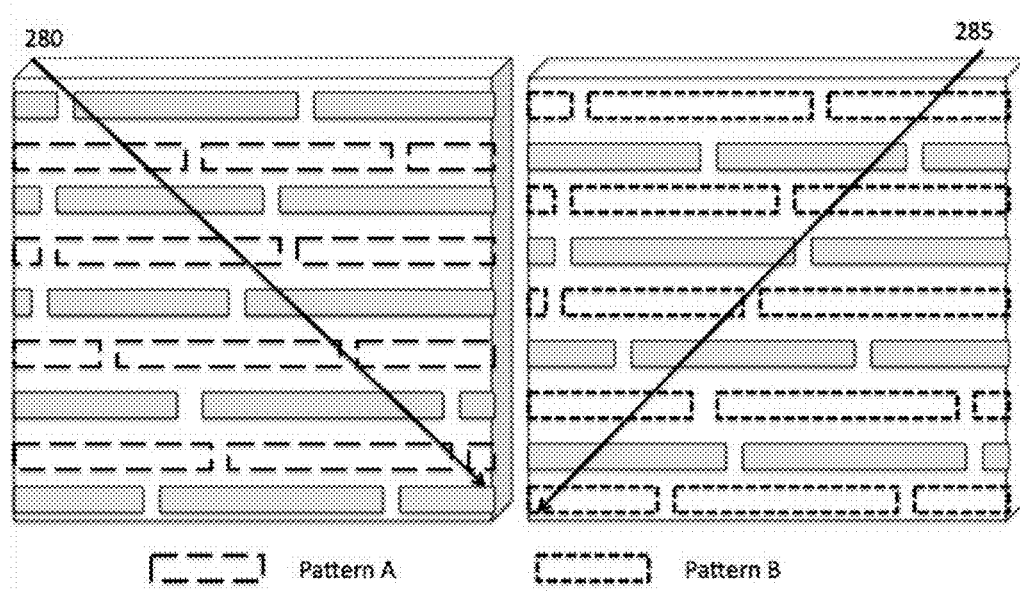
FIG. 38 is a schematic diagram illustrating the directional stagger of laser-cut Pattern A and Pattern B in one of the embodiments.

FIG. 38 is a schematic diagram illustrating the directional stagger of laser-cut Pattern A and Pattern B in one of the embodiments.

Figure 39:
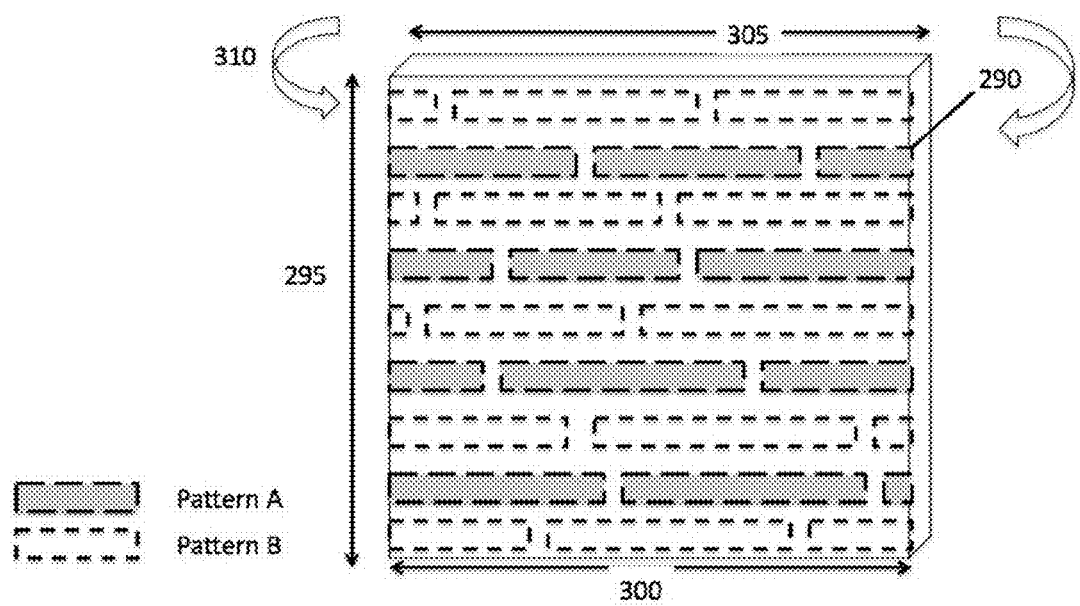
FIG. 39 is a schematic diagram illustrating the interspersed laser-cut Pattern A and B in one of the embodiments.

FIG. 39 is a schematic diagram illustrating the interspersed laser-cut Pattern A and B in one of the embodiments.

Figure 40:
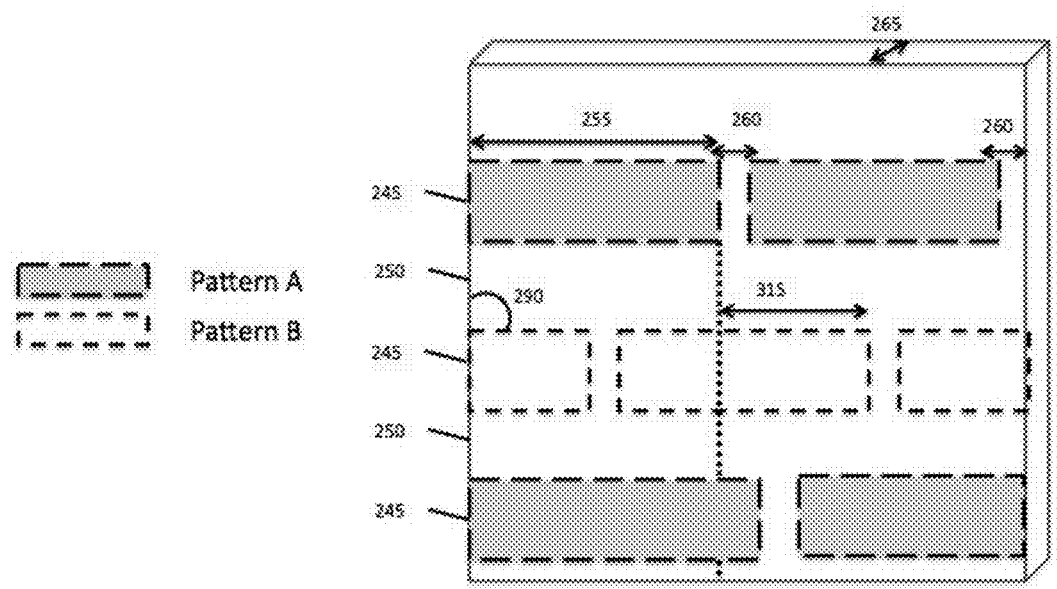
FIG. 40 is a schematic diagram illustrating the interspersed laser-cut Pattern A and B with the inter-pattern stagger in one of the embodiments.

FIG. 40 is a schematic diagram illustrating the interspersed laser-cut Pattern A and B with the inter-pattern stagger in one of the embodiments.

Figure 41:
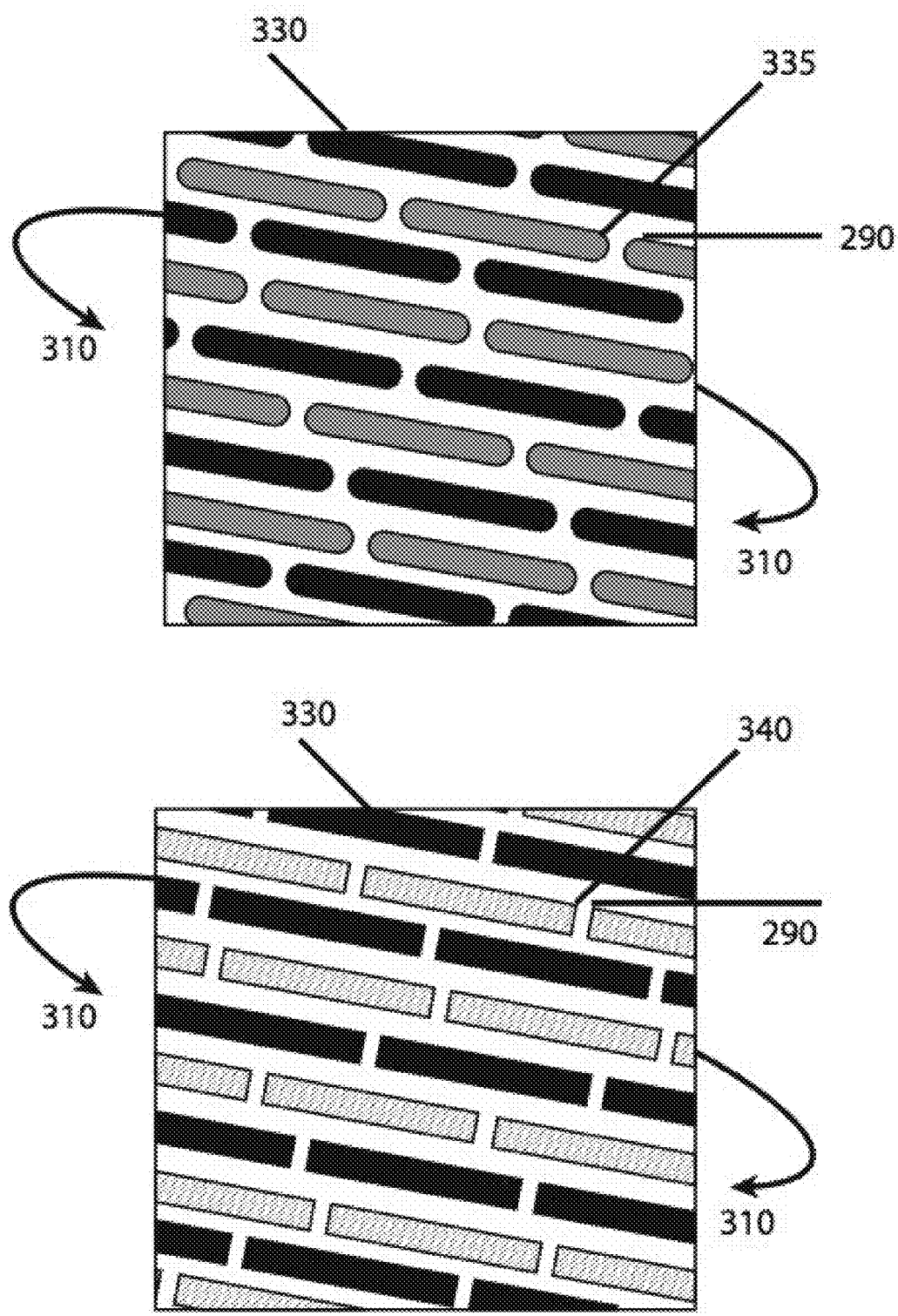
FIG. 41 is a schematic diagram illustrating the edges of the kerf in the angled laser-cut delivery system or hypotube are rounded or sharp in one of the embodiments.

FIG. 41 is a schematic diagram illustrating the edges of the kerf in the angled laser-cut delivery system or hypotube are rounded or sharp in one of the embodiments.

Figure 42:
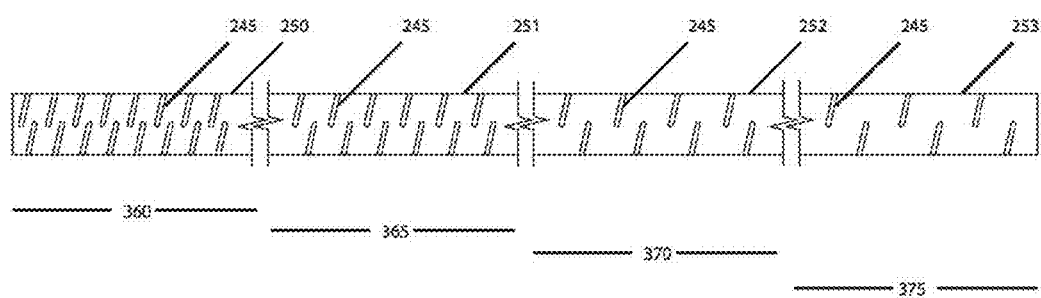
FIG. 42 is a schematic diagram illustrating the flexible transition points in the laser-cut pattern of the hypotube in one of the embodiments.

FIG. 42 is a schematic diagram illustrating the flexible transition points in the laser-cut pattern of the hypotube in one of the embodiments.

Figure 43:
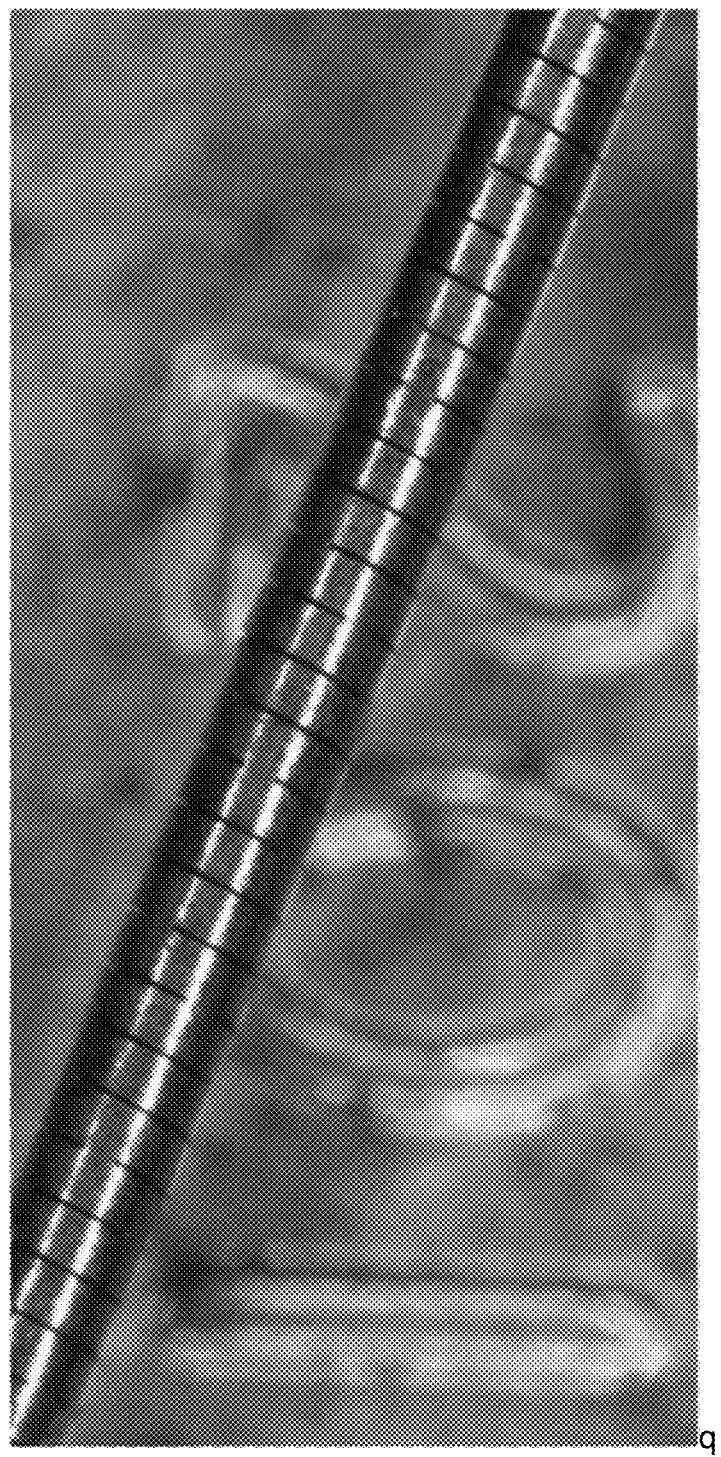
FIG. 43 is a photograph illustrating the degree of angled laser-cut and the degree of uncut in the angled laser-cut delivery system or hypotube in one of the embodiments.

FIG. 43 is a photograph illustrating the degree of angled laser-cut and the degree of uncut in the angled laser-cut delivery system or hypotube in one of the embodiments.

Figure 44:
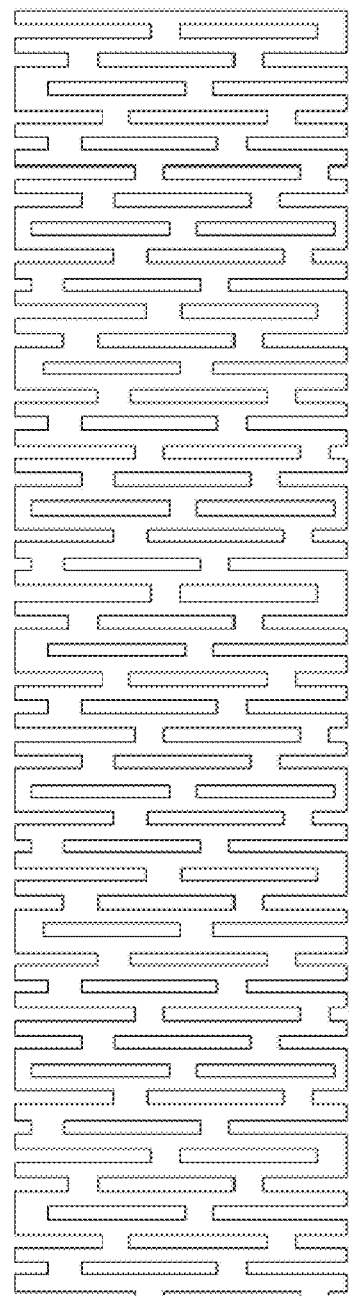
FIG. 44 is a schematic diagram illustrating the horizontal laser-cut delivery system in one of the embodiments.

FIG. 44 is a schematic diagram illustrating the horizontal laser-cut delivery system in one of the embodiments.

Figure 45:
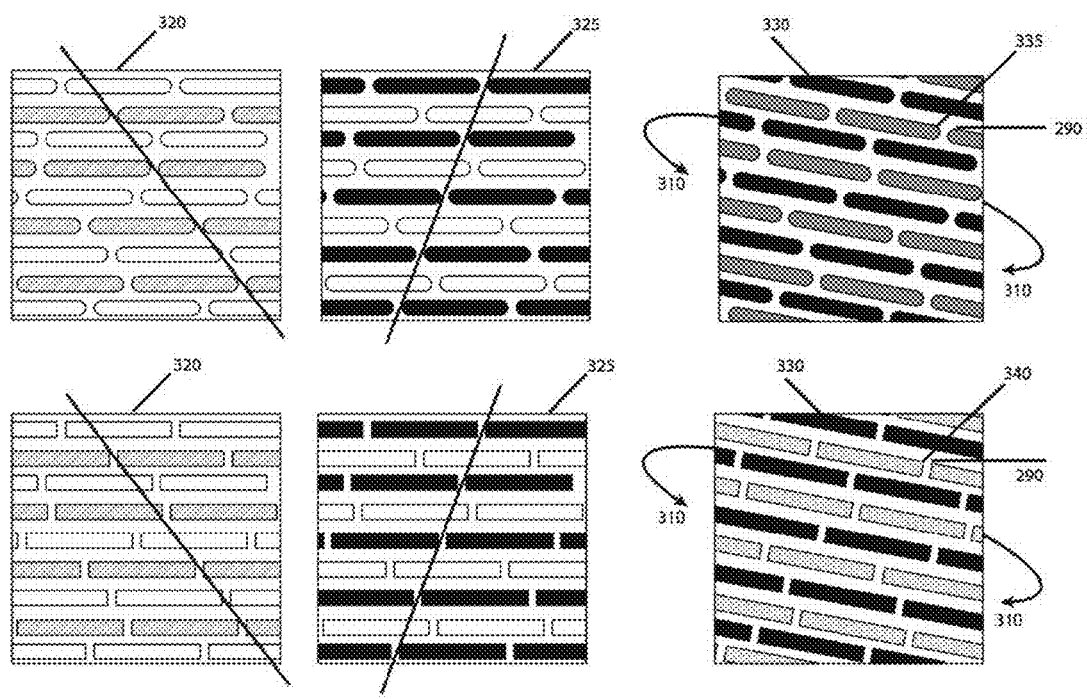
FIG. 45 is a schematic diagram illustrating the edges of the kerf in the horizontal laser-cut delivery system or hypotube are rounded or sharp in one of the embodiments.

FIG. 45 is a schematic diagram illustrating the edges of the kerf in the horizontal laser-cut delivery system or hypotube are rounded or sharp in one of the embodiments.

Figure 46:
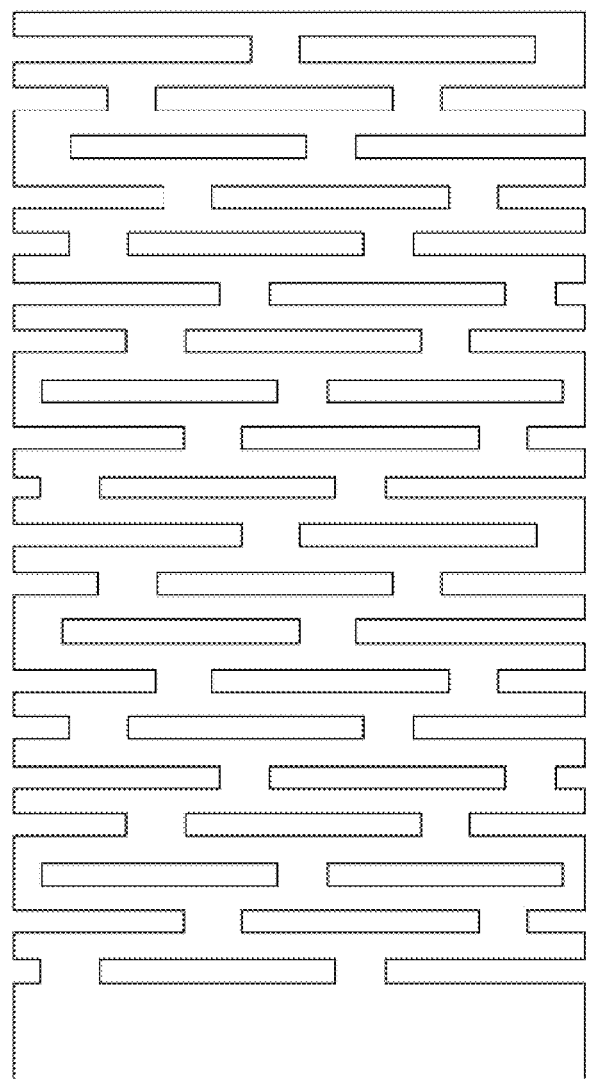
FIG. 46 is a photograph illustrating the degree of horizontal laser-cut and the degree of uncut in the horizontal laser-cut delivery system or hypotube in one of the embodiments.

FIG. 46 is a photograph illustrating the degree of horizontal laser-cut and the degree of uncut in the horizontal laser-cut delivery system or hypotube in one of the embodiments.

Figure 47:
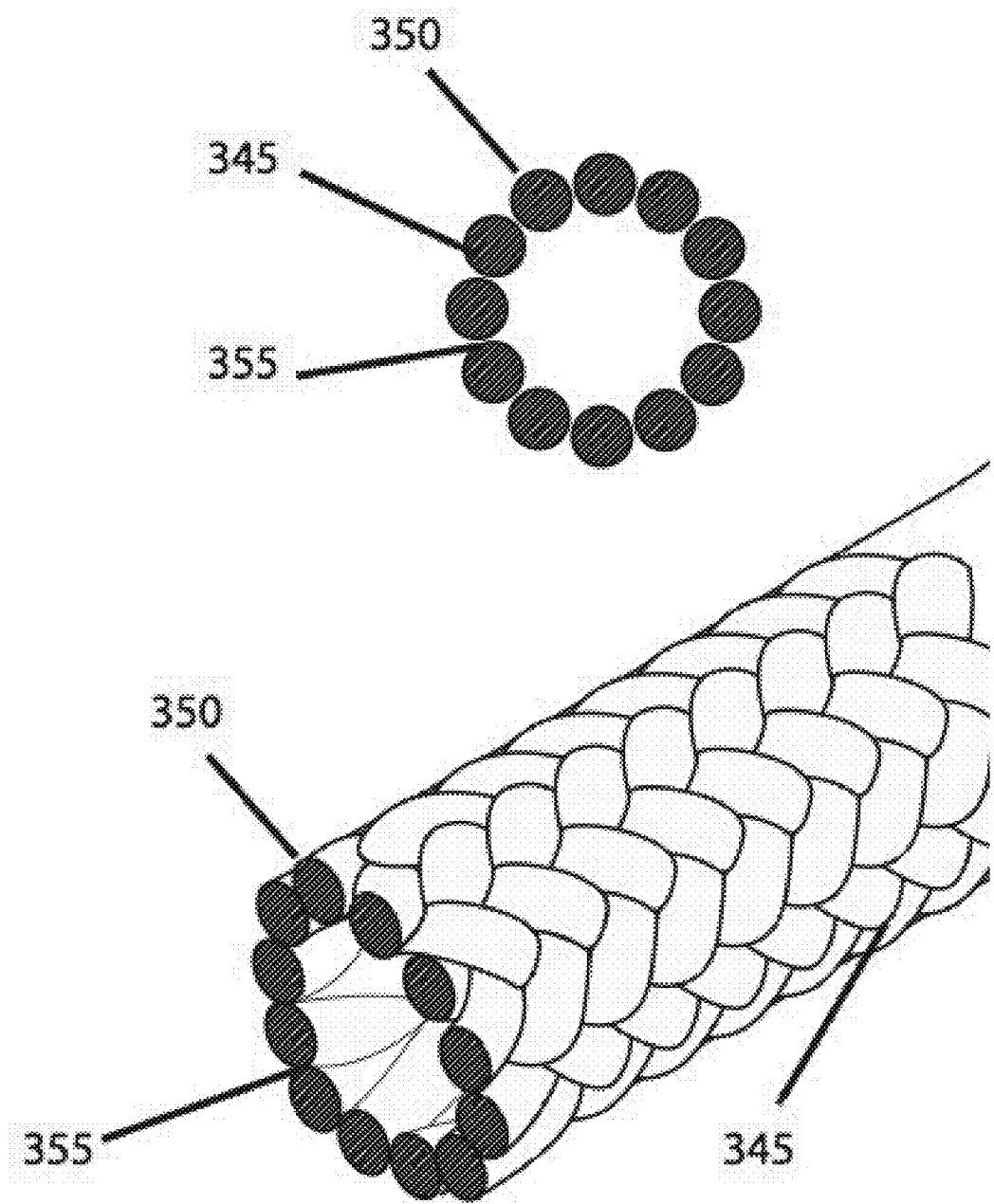
FIG. 47 is a schematic diagram illustrating a hybrid delivery system with the filaments or wires that are braided together like a hypotube in one of the embodiments.

FIG. 47 is a schematic diagram illustrating a hybrid delivery system with the filaments or wires that are braided together like a hypotube in one of the embodiments.

Figure 48:
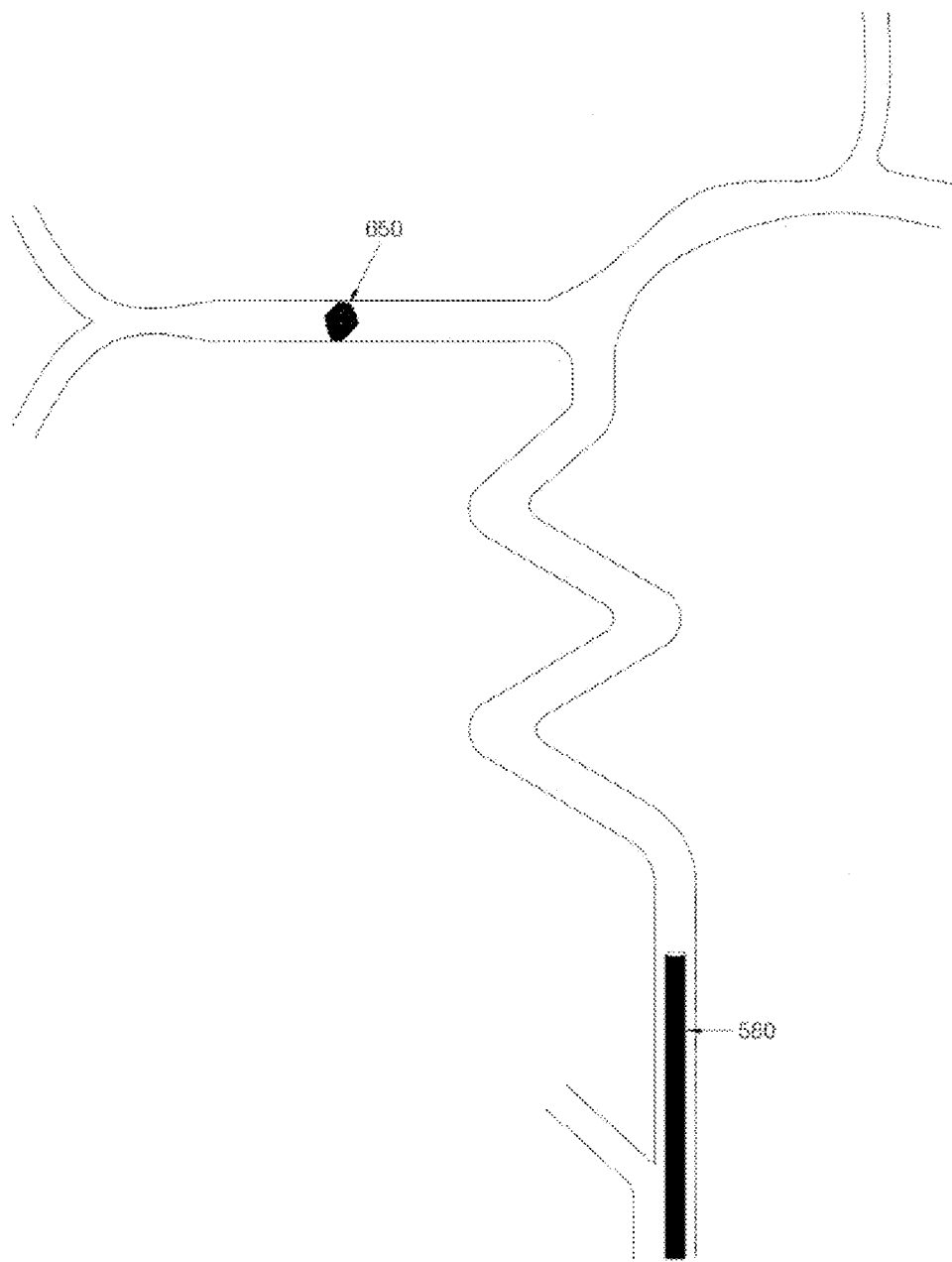
FIG. 48 is a schematic diagram illustrating a thrombus or blood clot in the right middle cerebral artery causing an acute ischemic stroke noted during angiography with a guide catheter or a shuttle or a balloon guide catheter positioned in the right internal carotid artery in one of the embodiments.

FIG. 48 is a schematic diagram illustrating a thrombus or blood clot in the right middle cerebral artery causing an acute ischemic stroke noted during angiography with a guide catheter or a shuttle or a balloon guide catheter positioned in the right internal carotid artery in one of the embodiments.

Figure 49:
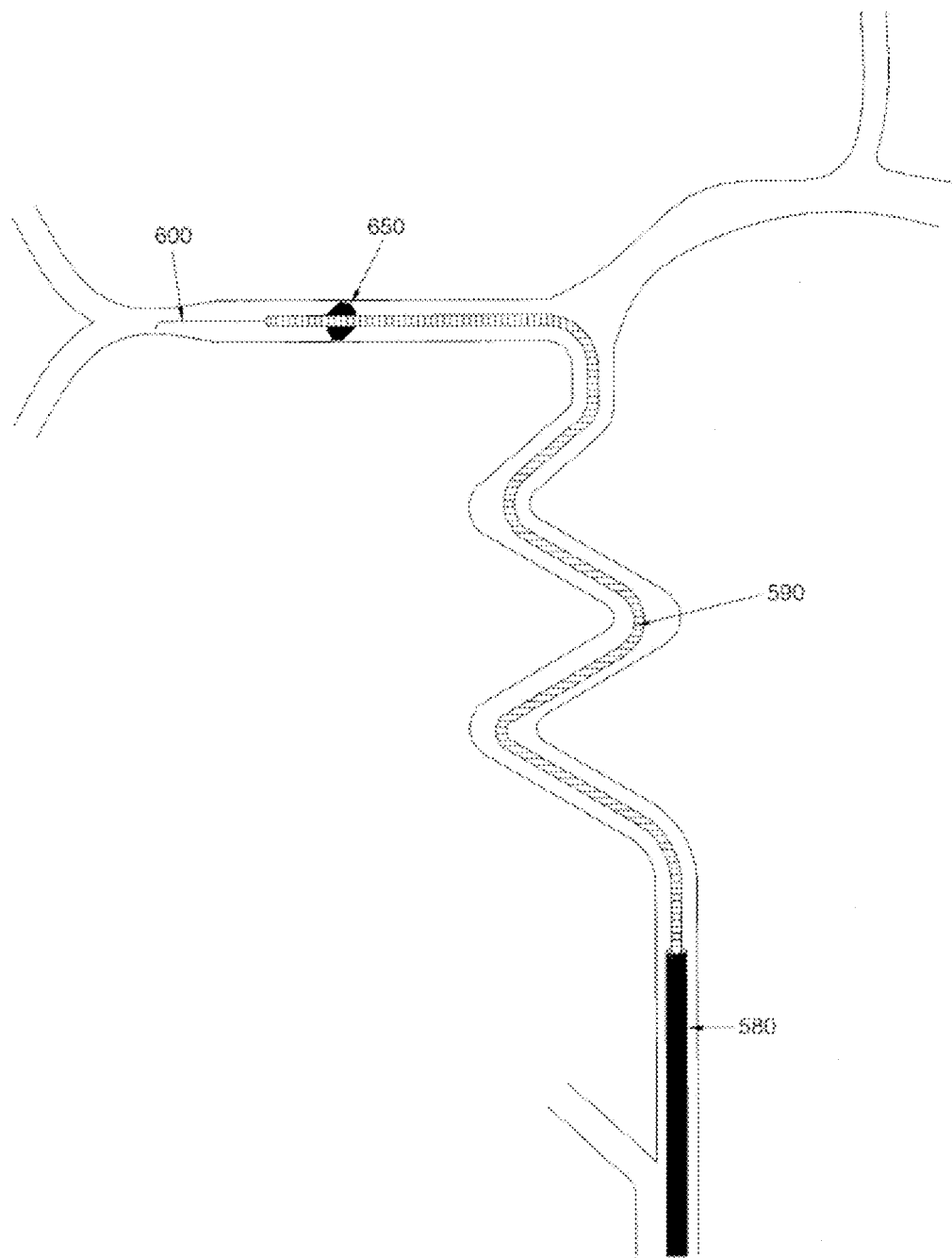
FIG. 49 is a schematic diagram illustrating a standard microcatheter being advanced across the thrombus or blood clot in the right middle cerebral artery over a microwire in one of the embodiments.

FIG. 49 is a schematic diagram illustrating a catheter (e.g., microcatheter) being advanced across the thrombus or blood clot in the right middle cerebral artery over a microwire in one of the embodiments. The microwire is then removed and the mechanical thrombectomy device is advanced through the hub of the microcatheter via an introducer sheath that is protective encasing for the flexible delivery system. In several embodiments, the catheter (e.g., microcatheter) is reinforced with the laser cut hypotube so as to, in one embodiment, inherit the maneuverability advantages of the hypotube (e.g., to facilitate proximal support and distal flexibility). In some embodiments, a catheter with varying pitches is used. For example, the pitch from the distal end to the proximal end varies as follows: about 0.005 inch, 0.01 inch, 0.02 inch, 0.04 inch, 0.08 inch and 0.16 inch. In some embodiments, the pitch from the distal end to the proximal end varies as follows: about 0.005 inch for the distal most 20%, 0.01 inch for the next 15%, 0.02 inch for the next 15%, 0.04 inch for the next 15%, 0.08 inch for the next 15%, and 0.16 inch for the next (or proximal-most) 20%.

The introducer sheath may comprise a biomedical polymer, e.g., silicone, polyurethane, polyethylene (Rexell™ made by Huntsman), polypropylene, polyester (Hytril™ made by Dupont), poly tetra fluoro-ethylene (PTFE), polyvinyl chloride (PVC), polyamides (Durethan™ made by Bayer), polycarbonate (Corethane™ made by Corvita Corp), or polyethylene-terephthalate. Combinations of two or more of these materials may also be used.

The microcatheter may comprise a biomedical polymer, e.g., silicone, polyurethane, polyethylene (Rexell™ made by Huntsman), polypropylene, polyester (Hytril™ made by Dupont), poly tetra fluoro-ethylene (PTFE), polyvinyl chloride (PVC), polyamides (Durethan™ made by Bayer), polycarbonate (Corethane™ made by Corvita Corp), or polyethylene-terephthalate. Combinations of two or more of these materials may also be used.

Figure 50:
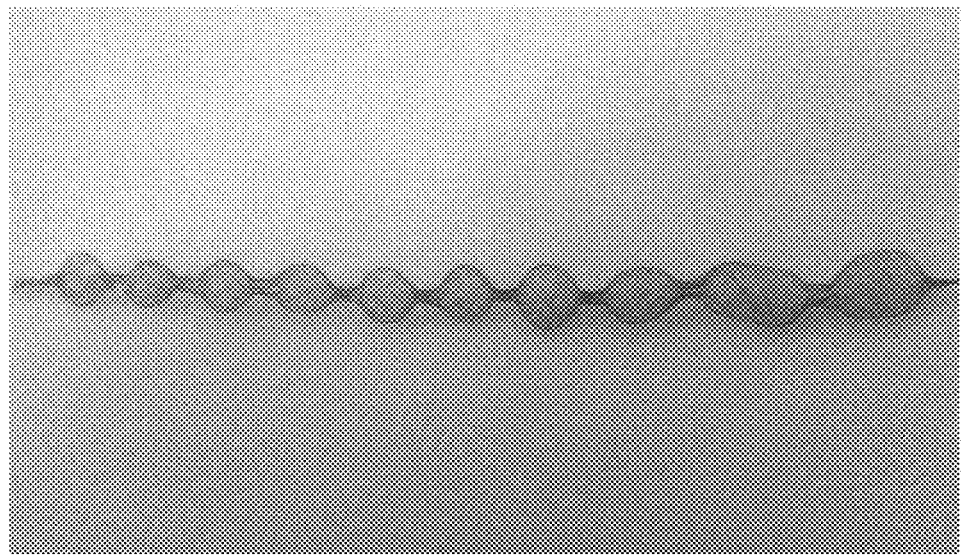
FIG. 50 is a photograph illustrating the shape-set textile structure based mechanical thrombectomy device in one of the embodiments.

FIG. 50 is a photograph illustrating the shape-set textile structure based mechanical thrombectomy device in one of the embodiments.

In several embodiments, the devices described herein can be used in the brain. In some embodiments, vasculature in the periphery can be treated. In some embodiments, coronary vessels are treated. Abdominal aorta and branches are treated in several embodiments.

In some embodiments, a subject having a clot is identified. An access catheter is advanced over a guidewire to a vessel proximate or containing the clot. The guidewire may be removed at this stage. A microcatheter is advanced over a microwire, but stop before or at the clot. The microwire then crosses the clot by 0.5-5 mm (e.g., slices through the center of the clot). The microcatheter is then advanced over the microwire to cross the clot. The microwire is then removed or retracted. The thrombectomy device (the elongate support structure with the bulbs bonded to a delivery system, such as a hypotube, wire or multi-filament wire/hypotube device), as disclosed in several embodiments herein is positioned within an introducer sheath, and together are advanced through the hub of the microcatheter. The thrombectomy device is then advanced through the microcatheter, and the introducer sheath is removed. The thrombectomy device is advanced until it is at the tip of the microcatheter (which is beyond the clot). The thrombectomy device is kept in position, and the microcatheter is retracted (e.g., unsleeved, unsheathed) until the thrombectomy device is expanded. The length of retraction is related to length of the clot in one embodiment (e.g., the microcatheter is retracted to or before the proximal end of the clot). The thrombectomy device is torqued (e.g., in a counterclockwise motion) to facilitate torsional rasping (e.g., rotationally scraping), thereby allowing the bulb(s) to entrap the clot, and collect any debris (emboli). The sticky portions of the clot, which can be attached to the endothelium wall, can be removed by the torquing motion. The non-laser cut braided nature of the bulbs facilaite gentle entrapment of the clot without perforating the blood vessel. In one embodiment, a 360 degree rotation on the proximal end results in a distal rotation that is less than 360 degrees (e.g., 90-180 degrees). In several embodiments, the rotational force from the proximal end to the distal is not 1:1. Instead the ratio is 1:0.75, 1:0.5 or 1:0.25. This non-1:1 ratio, in some embodiments, is beneficial because it provides a gentle rotation that reduces the risk that the blood vessel is rotated, displaced, disrupted or perforated. In several embodiments, if one bulb cannot fully entrap the clot, another bulb (whether it is the same or different in size and/or shape) will be able to further entrap the clot. In some embodiments, the undulations (e.g., the hills and valleys created by the bulbs and support structure) facilitate clot entrapment. Undulation is also provided at a micro level by the braiding pattern. This dual-undulating pattern enhances scraping and entrapment in several embodiments. The clot, once entrapped or captured by the bulbs, can then be removed as the thrombectomy device is removed from the subject. The thrombectomy device is removed as follows in some embodiments: the microcatheter and the delivery system (e.g., hypotube) are retracted into the tip of the guide catheter while negative suction is applied (e.g., with a syringe) at the level of the guide catheter and also while the microcatheter is retracted at a similar rate such that the microcatheter does not generally recapture any expanded portion of the thrombectomy device or expand (or expose) additional portions of the thrombectomy device. In other words, unexpanded bulbs remain unexpanded and expanded bulbs remain expanded until they are retracted into the guide catheter. Suction can be applied for about 5-30 seconds using a 30-90 cc syringe. The steps above need not be performed in the order recited.

The following references are herein incorporated by reference: (1) Sarti C, Rastenyte D, Cepaitis Z, Tuomilehto J. International trends in mortality from stroke, 1968 to 1994. Stroke. 2000; 31:1588-1601; (2) Wolf P A, D'Agostino R B. Epidemiology of Stroke. In: Barnett H J M, Mohr J P, Stein B M, Yatsu F, eds. Stroke: Pathophysiology, Diagnosis, and Management. 3rd ed. New York, N.Y.: Churchill Livingstone; 1998:6-7; (3) Adams H P, Jr., Adams R J, Brott T, del Zoppo G J, Furlan A, Goldstein L B, Grubb R L, Higashida R, Kidwell C, Kwiatkowski T G, Marler J R, Hademenos G J. Guidelines for the early management of patients with ischemic stroke: A scientific statement from the Stroke Council of the American Stroke Association. Stroke. 2003; 34:1056-1083; (4) Rymer M M, Thrutchley D E. Organizing regional networks to increase acute stroke intervention. Neurol Res. 2005; 27:59-16; and (5) Furlan A, Higashida R, Wechsler L, Gent M, Rowley H, Kase C, Pessin M, Ahuj a A, Callahan F, Clark W M, Silver F, Rivera F. Intra-arterial prourokinase for acute ischemic stroke. The PROACT II study: a randomized controlled trial. Prolyse in Acute Cerebral Thromboembolism. Jama. 1999; 282:2003-2011.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the various embodiments described and the appended claims. The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers. For example, "about 3 mm" includes "3 mm."

What is claimed is:

1. A thrombectomy device comprising:
an elongate support structure comprising a plurality of shape-memory and radiopaque wires woven to form a textile fabric having a collapsed state and an expanded state, the elongate support structure comprising:
a plurality of self-expanding generally spherical bulbs in the expanded state comprising:

a first bulb;

a second bulb distal to the first bulb, the first bulb and the second bulb having a first diameter;

a third bulb distal to the second bulb;

a fourth bulb distal to the third bulb, the third bulb and the fourth bulb having a second diameter smaller than the first diameter;

a fifth bulb distal to the fourth bulb;

a sixth bulb distal to the fifth bulb;

a seventh bulb distal to the sixth bulb, the fifth bulb, the sixth bulb, and the seventh bulb having a third diameter smaller than the second diameter;

an eighth bulb distal to the seventh bulb;

a ninth bulb distal to the eighth bulb; and a tenth bulb distal to the ninth bulb, the eighth bulb, the ninth bulb, and the tenth bulb having a fourth diameter smaller than the third diameter, necks longitudinally between and radially inward of the self-expanding bulbs, and a distal neck distal to and radially inward of a distal-most bulb of the self-expanding bulbs, the distal neck comprising a coated distal end;

a delivery system comprising a hypotube comprising two longitudinally interspersed and circumferentially staggered cut patterns, the cut patterns each comprising a plurality of rows each comprising two longitudinally-spaced kerfs angled with respect to a longitudinal axis of the hypotube and comprising rounded edges, wherein a longitudinally-spacing of the kerfs varies along the hypotube; and a bonding zone where the delivery system is coupled to the elongate support structure, the bonding zone comprising a radiopaque marker band.

2. The device of claim 1, wherein an outer diameter of the elongate support structure in the collapsed state is less than about 0.0125 inches.

3. The device of claim 1, wherein an outer diameter of the elongate support structure in the collapsed state is in a range of about 0.1-0.9 mm.

4. The device of claim 1, wherein the first diameter is about 4.5 mm, the second diameter is about 4 mm, the third diameter is about 3.5 mm, and the fourth diameter is about 3 mm.

5. A thrombectomy device comprising:

an elongate support structure comprising a plurality of wires woven to form a textile fabric having a collapsed state and an expanded state, the elongate support structure comprising a plurality of longitudinally-spaced self-expanding bulbs in the expanded state, wherein the plurality of bulbs comprises five to ten bulbs, and wherein at least two of the plurality of bulbs have different outer diameters in the expanded state; and a delivery system comprising a hypotube comprising a plurality of longitudinally interspersed cut patterns each comprising a plurality of rows of longitudinally-spaced kerfs.

6. The device of claim 5, wherein the plurality of bulbs comprises ten bulbs.

7. The device of claim 5, wherein at least two of the plurality of bulbs have different shapes in the expanded state.

8. The device of claim 5, wherein at least one of the plurality of bulbs has a spherical shape in the expanded state.

9. The device of claim 5, wherein at least one of the plurality of bulbs has a oblong shape in the expanded state.

10. The device of claim 5, wherein longitudinal spacing between the plurality of bulbs is constant.

11. The device of claim 5, wherein the plurality of wires comprises shape memory and radiopaque wires.

12. The device of claim 11, wherein the radiopaque wires are clustered to enhance visibility under x-ray.

13. The device of claim 5, wherein an outer diameter of the elongate support structure in the collapsed state is less than about 0.0125 inches.

14. The device of claim 5, wherein each of the rows is angled with respect to a longitudinal axis of the hypotube.

15. The device of claim 5, wherein the kerfs comprise rounded edges.

16. The device of claim 5, wherein the plurality of bulbs comprises five bulbs.

17. The device of claim 5, wherein the plurality of bulbs comprises six bulbs.

18. The device of claim 5, wherein the outer diameters of the plurality of bulbs are tapered from a largest outer diameter of the proximal-most bulb to a smallest outer diameter of a distal-most bulb.

19. The device of claim 5, wherein the plurality of wires comprises a first plurality of wires comprising shape-memory material and a second plurality of wires comprising radiopaque material.

20. The device of claim 19, wherein at least some of the second plurality of wires are grouped to form a radiopaque band under fluoroscopy.

* * * * *